United States Patent
Hasegawa et al.

(10) Patent No.: US 10,460,075 B2
(45) Date of Patent: Oct. 29, 2019

(54) INFORMATION PROCESSING APPARATUS AND METHOD TO MOVE A DISPLAY AREA OF A NEEDLE BIOPSY IMAGE

(71) Applicant: Sony Corporation, Tokyo (JP)

(72) Inventors: Yutaka Hasegawa, Kanagawa (JP); Hidaka Uchida, Tokyo (JP); Yoichi Mizutani, Saitama (JP); Shigeatsu Yoshioka, Kanagawa (JP); Masato Kajimoto, Chiba (JP); Kouji Ogura, Kanagawa (JP); Masashi Kimoto, Tokyo (JP); Naoki Tagami, Tokyo (JP); Toru Mitome, Tokyo (JP)

(73) Assignee: Sony Corporation, Tokyo (JP)

( * ) Notice: Subject to any disclaimer, the term of this patent is extended or adjusted under 35 U.S.C. 154(b) by 162 days.

(21) Appl. No.: 14/405,699

(22) PCT Filed: May 21, 2013

(86) PCT No.: PCT/JP2013/003229
§ 371 (c)(1),
(2) Date: Dec. 4, 2014

(87) PCT Pub. No.: WO2013/186995
PCT Pub. Date: Dec. 19, 2013

(65) Prior Publication Data
US 2015/0169826 A1 Jun. 18, 2015

(30) Foreign Application Priority Data

Jun. 14, 2012 (JP) ................. 2012-134441

(51) Int. Cl.
*G06F 19/00* (2018.01)
*G06F 3/0485* (2013.01)
(Continued)

(52) U.S. Cl.
CPC ........ *G06F 19/321* (2013.01); *A61B 10/0233* (2013.01); *G06F 3/0485* (2013.01);
(Continued)

(58) Field of Classification Search
None
See application file for complete search history.

(56) References Cited

U.S. PATENT DOCUMENTS

| 5,745,098 A | 4/1998 | Yamaji | |
|---|---|---|---|
| 6,331,116 B1 * | 12/2001 | Kaufman | G06K 9/209 345/418 |

(Continued)

FOREIGN PATENT DOCUMENTS

| JP | 07-152528 | 6/1995 |
|---|---|---|
| JP | 2001-510894 A | 8/2001 |

(Continued)

OTHER PUBLICATIONS

International Search Report issued in connection with International Patent Application No. PCT/JP2013/003229, dated Jul. 2, 2013. (1 page).

(Continued)

*Primary Examiner* — Stella Higgs
(74) *Attorney, Agent, or Firm* — Chip Law Group

(57) ABSTRACT

To provide an information processing apparatus, an information processing method, and an information processing program that allow a user to easily adequately move a display area by guiding a browsed part when a needle biopsy image is browsed.
[Solving Means] An information processing apparatus includes: a storage unit to store a pathological image of a specimen and guide information along the center line of a shape of the specimen in the pathological image; a display control unit to display at least a part of the stored pathological image, as an observation image, on a screen; an input unit to receive an instruction for changing a range on the pathological image of the observation image displayed on the screen, from a user; and a control unit to calculate the range on the pathological image of the observation image based on the instruction and the stored guide information.

17 Claims, 20 Drawing Sheets

(51) Int. Cl.
- *A61B 10/02* (2006.01)
- *G06F 3/0484* (2013.01)
- *G06T 7/13* (2017.01)
- *G06K 9/00* (2006.01)

(52) U.S. Cl.
CPC ..... *G06F 3/04842* (2013.01); *G06K 9/00127* (2013.01); *G06T 7/13* (2017.01); *G06T 2207/30021* (2013.01); *G06T 2207/30172* (2013.01)

(56) References Cited

U.S. PATENT DOCUMENTS

| | | | | |
|---|---|---|---|---|
| 2004/0167806 | A1* | 8/2004 | Eichhorn | G02B 21/26 705/3 |
| 2005/0078182 | A1* | 4/2005 | Lipsky | G06F 3/0481 348/143 |
| 2007/0276709 | A1* | 11/2007 | Trimby | A63F 13/00 705/6 |
| 2011/0060766 | A1* | 3/2011 | Ehlke | G06F 3/0481 707/802 |
| 2012/0005630 | A1* | 1/2012 | Ohba | G06F 3/1462 715/853 |

FOREIGN PATENT DOCUMENTS

| | | |
|---|---|---|
| JP | 2006-105695 A | 4/2006 |
| JP | 2006-519443 | 8/2006 |
| JP | 2010-061678 | 3/2010 |
| JP | 2014-520891 A | 8/2014 |

OTHER PUBLICATIONS

Extended European Search Report of EP Patent Application No. 17188574.2, dated Dec. 15, 2017, 27 pages.

Sudarsky, et al., "Slice-Based Guided Navigation for Colonography", XP-002758096, Medical Imaging 2007: Physiology, Function, and Structure from Medical Images, Proc. of SPIE vol. 6511, 65110T, 2007, 08 pages.

Roa-Pena, et al., "An Experimental Study of Pathologist's Navigation Patterns in Virtual Microscopy", Diagnostic Pathology 2010, 11 pages.

Romero, et al., "Virtual Microscopy in Medical Images: a Survey",Modern Research and Educational Topics in Microscopy, XP-002548368, pp. 996-1006.

Office Action for JP Patent Application No. 2017-012242, dated Dec. 5, 2017, 06 pages of Office Action and 04 pages of English Translation.

Extended European Search Report of EP Application No. 17188574. 2, dated Mar. 21, 2018, 19 pages of EESR.

Sudarsky, et al., "Slice-Based Guided Navigation for Colonography", Proceedings of SPIE, Medical Imaging 2007, Physiology, Function, and Structure from Medical, vol. 6511, 2007, 08 pages.

Roa-Pena, et al., "An Experimental Study of Pathologist's Navigation Patterns in Virtual Microscopy", Diagnostic Pathology, vol. 5, Issue 71, 2010, 11 pages.

Romero, et al., "Virtual Microscopy in Medical Images: a Survey", Modern Research and Educational Topics in Microscopy, FORMATEX, vol. 2, Jan. 2007, pp. 996-1006.

* cited by examiner

INFORMATION PROCESSING APPARATUS AND METHOD TO MOVE A DISPLAY AREA OF A NEEDLE BIOPSY IMAGE

CROSS REFERENCES TO RELATED APPLICATIONS

The present application is a national stage of International Application No. PCT/JP2013/003229 filed on May 21, 2013 and claims priority to Japanese Patent Application No. 2012-134441 filed on Jun. 14, 2012, the disclosure of which is incorporated herein by reference.

BACKGROUND

The present technology relates to an information processing apparatus, an information processing method, and an information processing program, by which a browsed part is guided when a needle biopsy image is viewed.

In a conventional browsing method, a client viewer has read and displayed images divided in a tile form and accumulated in an image server (tile images) according to a navigation operation instruction by a user. The user only needs to select a part desired to be viewed so that the system can recognize and display a corresponding tile image.

Further, for example, Patent Document 1 discloses the following technology. First, the client viewer requests image data from a virtual slide image file in a specific resolution. Next, a server system acquires a compressed block of image data including image data having a resolution close to the requested resolution and transmits this data block to the client. Subsequently, the client rescales the image data and presents an image in the requested resolution.

Patent Document 1: Japanese Patent Application Laid-open No. 2006-519443

SUMMARY

Problem to be Solved by the Invention

However, in the case where the needle biopsy image is viewed using the conventional browsing method, a navigation operation by the user has an excessive degree of freedom, and it has been difficult to adequately move a display area along a direction of the elongated specimen.

In view of the circumstances as described above, it is an object of the present technology to provide an information processing apparatus, an information processing method, and an information processing program that allow a user to easily adequately move a display area by guiding a browsed part when a needle biopsy image is browsed.

Means for Solving the Problem (1) In order to achieve the object described above, according to an embodiment of the present technology, there is provided an information processing apparatus including: a storage unit to store a pathological image of a specimen and guide information along the center line of a shape of the specimen in the pathological image; a display control unit to display at least a part of the stored pathological image, as an observation image, on a screen; an input unit to receive an instruction for changing a range on the pathological image of the observation image displayed on the screen, from a user; and a control unit to calculate the range on the pathological image of the observation image based on the instruction and the stored guide information.

In the present technology, unlike a conventional method of changing the range on the pathological image of the observation image based on only the scroll instruction input by the user, the range on the pathological image of the observation image is determined depending on the guide information, while taking into account the scroll instruction from the user. The guide information plays an important role when the range of the observation image on the pathological image is determined. For that reason, it is important how to determine the guide information with respect to the shape of the specimen. Since the guide information is set so as to obtain the observation image along the center line of the shape of the specimen, even when the user as an observer of the pathological image inputs a rough instruction to change the range of the observation image, the information processing apparatus appropriately calculates the range of the observation image along the center line of the shape of the specimen.

With this configuration, for example, in the case of a specimen elongated in an upper and lower direction, the user only has to roughly input "upper direction" or "lower direction" as a scroll direction of the observation image. Since the scrolling along the shape of the specimen is performed by the information processing apparatus, and thus the user is released from a task to finely adjust the scroll direction. For that reason, the user can focus on a diagnosis of the pathological image.

(2) Further, in order to achieve the object described above, in the information processing apparatus according to the embodiment of the present technology, the guide information may be configured to be an arrangement of positional information on the pathological image, the positional information including points that are set on the entire specimen at predetermined intervals on the center line of the specimen on the pathological image.

With this configuration, since the guide information is a sequence of points set on the center line of the specimen, the range of the observation image can be easily determined at a position along the center line of the specimen. Further, since the guide information is set on the entire specimen, when the range on the pathological image of the observation image is moved based on the guide information, the specimen can be observed from end to end. Thus, it is possible to prevent a pathologist as an observer from overlooking a part of area of the specimen.

(3) Further, in order to achieve the object described above, in the information processing apparatus according to the embodiment of the present technology, the control unit may be configured to assume the center point of the range on the pathological image of the observation image, as a first center point, the range being calculated based on only the instruction, and assume a point corresponding to the first center point and being on a line segment connecting adjacent points included in the guide information, as a second center point, to calculate the range on the pathological image of the observation image including the second center point.

With this configuration, even when an operation instruction is roughly made by the user, the range of the observation image can be corrected to a range along the guide information.

(4) Further, in order to achieve the object described above, in the information processing apparatus according to the embodiment of the present technology, the control unit may be configured to assume a point that is on the line segment and is the closest to the first center point, as the second center point.

With this configuration, even when the shape of the specimen imaged on the pathological image is elongated in the vertical direction or in the horizontal direction, the range based on the guide information corresponding to the instruction by the user can be set as the range of the observation image by using the same algorithm.

(5) Further, in order to achieve the object described above, in the information processing apparatus according to the embodiment of the present technology, the control unit may be configured to assume, as the second center point, a point that is the closest to the first center point among points at which auxiliary lines extended from the first center point in a horizontal direction and a vertical direction intersect the line segment.

With this configuration, the range based on the guide information corresponding to the instruction by the user can be calculated by using a simple algorithm.

(6) Further, in order to achieve the object described above, in the information processing apparatus according to the embodiment of the present technology, the control unit may be configured to prefetch the observation image from the storage unit, the observation image being predicted based on the guide information and the instruction predicted to be received by the input unit.

With this configuration, the prefetch cache hit ratio is very high. This is because the range of the observation image is previously determined by the guide information and the range of the observation image to be displayed next can be easily predicted. Since the hit ratio is very high, the observation image can be displayed at high speed. In particular, in the case where the information processing apparatus is in a low throughput environment, the feeling of use on the display of the observation image can be improved.

(7) Further, in order to achieve the object described above, in the information processing apparatus according to the embodiment of the present technology, the control unit may be configured to switch between a guide mode in which the range on the pathological image of the observation image is calculated based on the instruction and the guide information, and a normal mode in which the range on the pathological image of the observation image is calculated based on only the instruction.

With this configuration, the pathologist as a user can focus on an observation of the pathological image by roughly making an operation instruction and also move the display of the pathological image as the pathologist wants for observation.

(8) Further, in order to achieve the object described above, in the information processing apparatus according to the embodiment of the present technology, the control unit may be configured to switch between the guide mode and the normal mode based on a mode switching instruction that is explicitly made by the user and received by the input unit.

With this configuration, the user as a pathologist can perform an observation of the pathological image by reliably switching between the two modes.

(9) Further, in order to achieve the object described above, in the information processing apparatus according to the embodiment of the present technology, the control unit may be configured to assume, as a first input method, a method of inputting the instruction received by the input unit in the guide mode and assume, as a second input method, a method of inputting the instruction that is different from the first input method and is received by the input unit in the normal mode, determine by which of the input methods the instruction is input, and switch between the guide mode and the normal mode based on the determination.

With this configuration, time and effort for the user as a pathologist to switch between the two modes can be omitted.

(10) Further, in order to achieve the object described above, in the information processing apparatus according to the embodiment of the present technology, the display control unit may be configured to display an arrow indicating a position and a direction followed by a part of the specimen that deviates from the observation image, on the screen on which a part of the specimen is displayed as the observation image.

With this configuration, the user as a pathologist can previously know in which direction the range on the pathological image of the observation image moves based on the guide information.

(11) Further, in order to achieve the object described above, in the information processing apparatus according to the embodiment of the present technology, the display control unit may be configured to display the guide information on the screen.

With this configuration, the user as a pathologist can previously know in which direction the range on the pathological image of the observation image moves based on the guide information.

(12) Further, in order to achieve the object described above, in the information processing apparatus according to the embodiment of the present technology, the display control unit may be configured to display the guide information on a thumbnail map in which the entire pathological image is displayed.

With this configuration, the user as a pathologist can previously know in which direction the range on the pathological image of the observation image moves based on the guide information. Further, in the case where the user does not move the range of the observation image based on the guide information, an instruction to move the range can be given with the arrow as an index.

(13) Further, in order to achieve the object described above, the information processing apparatus according to the embodiment of the present technology may further include a controller including a tilt sensor, in which the user may input the instruction by tilting the controller.

With this configuration, for example, by tilting the controller, the user as a pathologist can perform an operation similar to an operation of the microscope, such as continuously moving the range of the observation image on the pathological image in one direction. Thus, it is possible to improve an affinity for a pathological diagnosis.

(14) Further, in order to achieve the object described above, in the information processing apparatus according to the embodiment of the present technology, the guide information may be configured to cause, in a case where a plurality of specimens are imaged on the pathological image, the control unit to calculate the range on the pathological image such that the observation image of an end of one of the specimens is followed by an end of another specimen to be the observation image.

With this configuration, the user as a pathologist can omit time and effort to move the range of the observation image manually, among the plurality of specimens imaged on the pathological image.

(15) Further, in order to achieve the object described above, according to an embodiment of the present technology, there is provided an information processing method including: storing, by a storage unit, a pathological image of a specimen and guide information along the center line of a shape of the specimen in the pathological image; displaying, by a display control unit, at least a part of the stored pathological image, as an observation image, on a screen; receiving, by an input unit, an instruction for changing a range on the pathological image of the observation image displayed on the screen, from a user; and calculating, by a control unit, the range on the pathological image of the observation image based on the instruction and the stored guide information.

(16) Further, in order to achieve the object described above, according to an embodiment of the present technology, there is provided an information processing program causing a computer to operate as: a storage unit to store a pathological image of a specimen and guide information along the center line of a shape of the specimen in the pathological image; a display control unit to display at least a part of the stored pathological image, as an observation image, on a screen; an input unit to receive an instruction for changing a range on the pathological image of the observation image displayed on the screen, from a user; and a control unit to calculate the range on the pathological image of the observation image based on the instruction and the stored guide information.

(17) Further, in order to achieve the object described above, according to an embodiment of the present technology, there is provided an information processing system including: a server computer including a storage unit to store a pathological image of a specimen and guide information along the center line of a shape of the specimen in the pathological image, and a providing unit to provide the stored pathological image and the stored guide information to a client computer; and the client computer including an acquiring unit to acquire the pathological image and the guide information from the server computer, a display control unit to display at least a part of the acquired pathological image, as an observation image, on a screen, an input unit to receive an instruction for changing a range on the pathological image of the observation image displayed on the screen, from a user, and a control unit to calculate the range on the pathological image of the observation image based on the instruction and the acquired guide information.

Effect of the Invention

As described above, according to the present technology, it is possible to allow a user to easily adequately move a display area by guiding a browsed part when a needle biopsy image is browsed.

Additional features and advantages are described herein, and will be apparent from the following Detailed Description and the figures.

DETAILED DESCRIPTION

Hereinafter, an embodiment according to the present technology will be described with reference to the drawings.

[Regarding Needle Biopsy]

Needle biopsy is a diagnosis in which a needle is inserted into a human body, and a tissue that is taken as a specimen in a hole of the needle, is observed with a microscope. Since a needle is used, the specimen placed on a glass slide has an elongated and linear shape. Normally, specimens obtained with a plurality of needles are arranged on one glass slide for observation, and thus a pathologist observes an image in which a plurality of elongated specimens are arranged.

The pathologist occasionally performs an observation by directly looking into a microscope, but as in this embodiment, there is another method of observing an image, which is captured using an imaging device attached to the microscope, as a virtual slide via a viewer computer. In the following description, it is assumed that the pathologist observes a pathological image captured as a virtual slide, by using the viewer computer.

Figure 1:
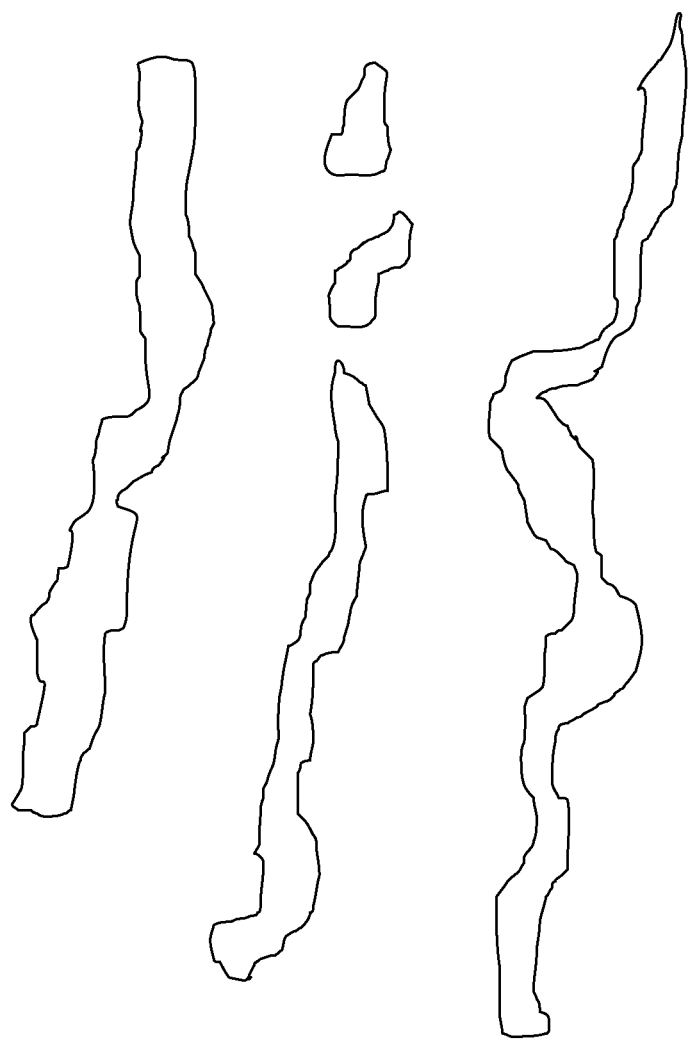
FIG. 1 A diagram showing an example of a virtual slide obtained by imaging a specimen of needle biopsy.

FIG. 1 is a diagram showing an example of a virtual slide obtained by imaging a specimen of needle biopsy. In this example, specimens obtained from three needles are arranged on a glass slide for imaging. The specimen at the center is taken from one needle, but it is broken at two points in midstream and thus divided into three parts.

[Regarding Usage Environment of Viewer Computer]

Figure 2:
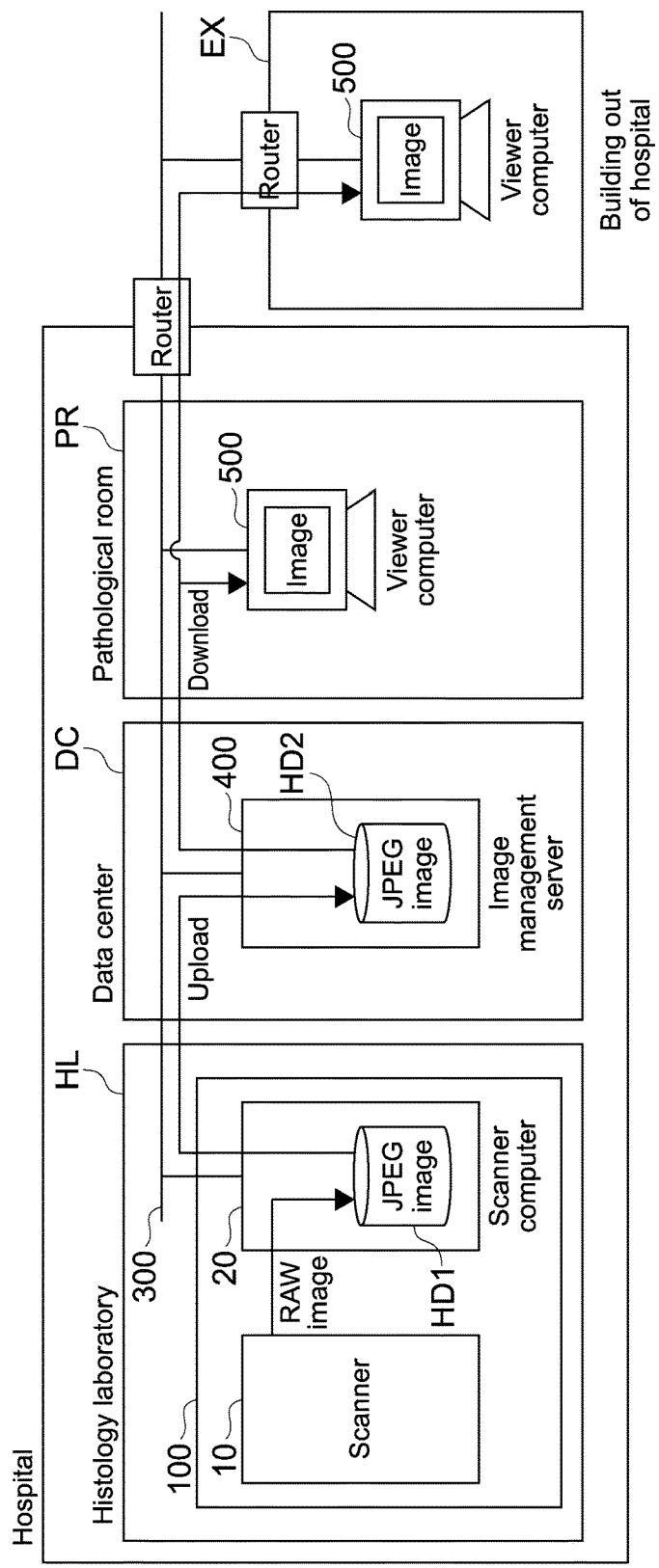
FIG. 2 A diagram showing a typical usage environment of a viewer computer according to the present technology.

FIG. 2 is a diagram showing a typical usage environment of a viewer computer 500 according to the present technology.

A scanner 100 including a microscope 10 and a scanner computer 20 is installed in a histology laboratory HL in a hospital. A RAW image captured with the microscope 10 is subjected to, in the scanner computer 20, image processing such as development processing, shading processing, color balance correction, gamma correction, and 8-bit conversion processing. Subsequently, the RAW image is divided in a tile form with 256 by 256 pixels, converted and compressed into a JPEG (Joint Photographic Experts Group) image, and then stored in a hard disk HD1.

Next, the JPEG image stored in the hard disk HD1 of the scanner computer 20 is uploaded, via a network 300, to a hard disk HD2 in an image management server 400 in a data center DC in the same hospital. The pathologist as an observer is in a pathological room PR in the hospital or in a building EX out of the hospital and uses a viewer computer 500 connected to the image management server 400 via the network 300 to observe the JPEG image stored in the hard disk HD2 of the image management server 400.

[Configuration of Viewer Computer 500]

Next, the configuration of the viewer computer 500 will be described.

Figure 3:
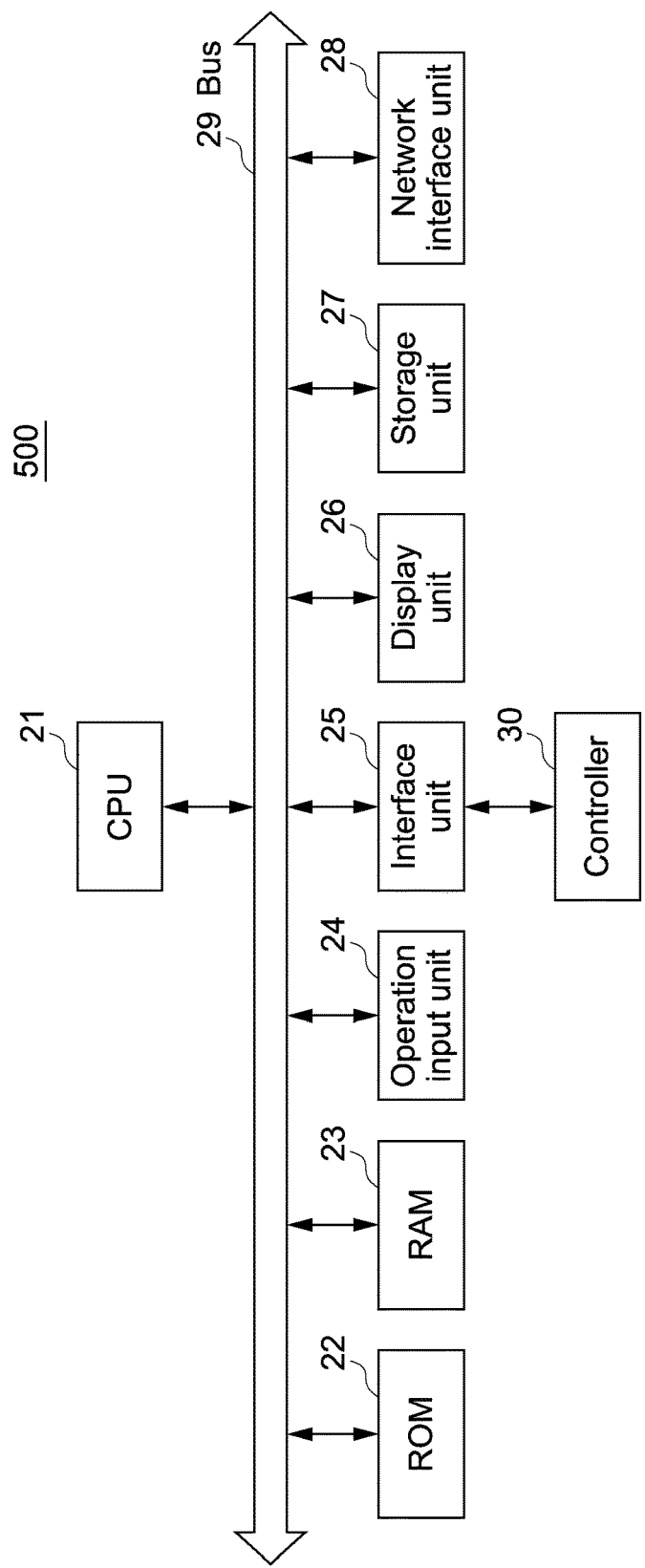
FIG. 3 A block diagram showing a hardware configuration of the viewer computer according to the present technology.

FIG. 3 is a block diagram showing a hardware configuration of the viewer computer 500 according to the present technology.

The viewer computer 500 includes a CPU (Central Processing Unit) 21 that performs arithmetic control, a ROM (Read Only Memory) 22, a RAM (Random Access Memory) 23 serving as a work memory of the CPU 21, an operation input unit 24 that inputs a command corresponding to an operation of a user, an interface unit 25, a display unit 26, a storage unit 27, a network interface unit 28, and a bus 29 that connects those components to one another.

In the ROM 22, programs for executing various types of processing are stored.

A controller 30 is connected to the interface unit 25. The controller 30 includes various buttons and sticks and can receive various inputs made by the user. Further, the controller 30 incorporates an acceleration sensor and a tilt sensor and can receive an instruction given to the controller 30 by the user tilting or shaking the controller 30.

The network 300 is connected to the network interface unit 28. A liquid crystal display, an EL (Electro Luminescence) display, a plasma display, or the like is applied to the display unit 26. A magnetic disc typified by an HDD (Hard Disk Drive), a semiconductor memory, an optical disc, or the like is applied to the storage unit 27.

The CPU 21 develops a program in the RAM 23, the program corresponding to a command given from the operation input unit 24 among a plurality of programs stored in the ROM 22, and controls the display unit 26 and the storage unit 27 as appropriate according to the developed program.

The CPU 21 achieves functional blocks that will be described later. The CPU 21 executes the programs stored in the ROM 22, the storage unit 27, and the like, to control the respective members described above as needed. Thus, the viewer computer 500 can achieve various functional blocks and operate the members described above as the viewer computer 500.

[Specific Example of Controller 30]

Figure 4:
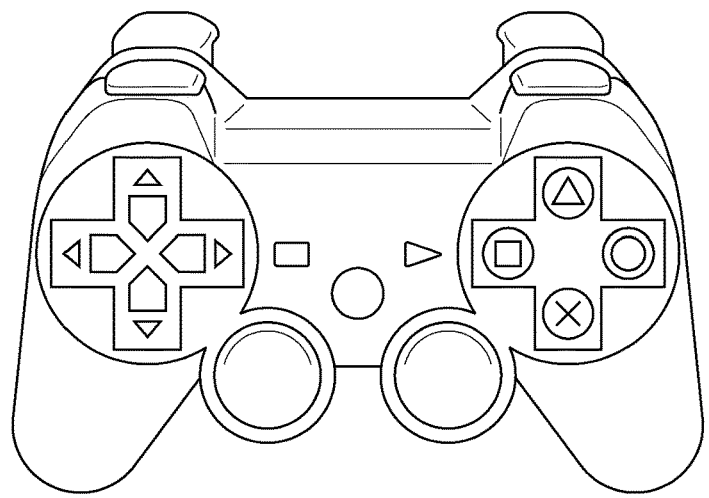
FIG. 4 A diagram showing a game controller, which is a specific example of a controller.

FIG. 4 is a diagram showing a game controller, which is a specific example of the controller 30. The controller 30 can be held by both hands, and buttons such as a cross key can be operated by the right and left index fingers and thumbs. Further, one stick for each side of the right and left, a total of two sticks are provided at spots where the right and left thumbs hit, and a direction over 360 degrees can be input.

It should be noted that as described above, since the controller 30 is provided with an acceleration sensor and a tilt sensor, various instructions can be input by shaking or tilting the main body of the controller 30.

[Advantage by Use of Controller 30]

Since a huge image is handled in a pathological diagnosis, there is an opportunity to successively give a lot of instructions to scroll a screen on which an image is displayed. At that time, when a mouse is used, for example, in the case where the image is scrolled by a drag, a drag operation has to be repeated many times.

In that regard, in the controller 30, if a continuous scroll operation is assigned to processing corresponding to an operation of holding the stick down in a certain direction or an operation of holding the main body of the controller 30 tilted by a certain amount, it is possible to easily continue scrolling. Further, since the continuous scroll operation is similar to an operation of the microscope, it has a high affinity for a pathological diagnosis.

Furthermore, in the pathological diagnosis, the pathologist wants to frequently rescale and scroll an image in a state of focusing on the image and keeping an eye on the image. For that reason, it is more effective to assign processing to the button or the stick of the controller 30 to directly perform an operation or assign processing to an operation of shaking or tilting the main body of the controller 30, than a menu operation with a mouse.

[Specific Example of Inputting Instruction with Controller 30]

Specific examples of inputting an instruction with the controller 30 are conceived as follows: vertically shake the controller 30 to enlarge an image; horizontally shake the controller 30 to horizontally scroll an image; obliquely shake the controller 30 to hide additional information displayed on a screen; tilt the controller 30 for only a moment to display the next image; operate a left-side stick of the controller 30 to divide the screen, and the like.

It should be noted that regarding a scroll mode that will be described later, operations in a normal mode and a guide mode can be assigned to the controller 30. For example, in the normal mode, the controller 30 is tilted, and thus the screen can be scrolled, and in the guide mode, a right-side stick of the controller 30 is tilted, and thus scrolling along a guide line that will be described later can be performed.

[Configuration of Image Management Server 400]

Next, the configuration of the image management server 400 will be described.

The hardware configuration of the image management server is basically the same as the hardware configuration of the viewer computer 500, excluding that the controller 30 is not connected. So, detailed description will be omitted.

[Functional Blocks of Image Management Server 400]

Figure 5:
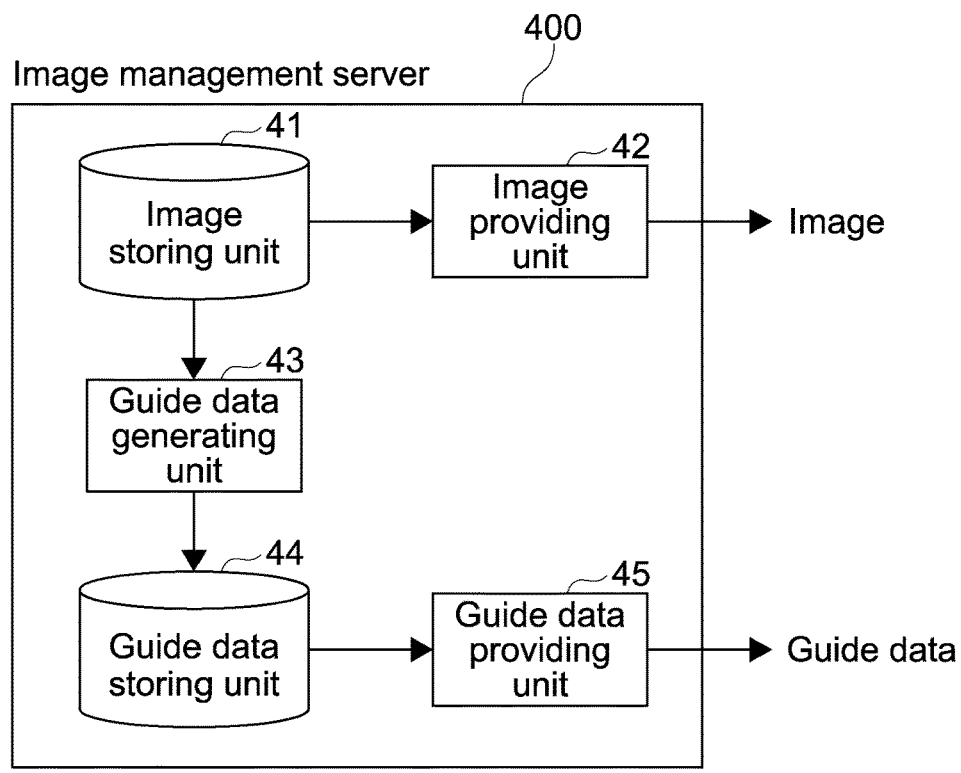
FIG. 5 A diagram showing the functional blocks of an image management server.

Next, the functional blocks of the image management server 400 will be described. The image management server 400 has a main function of providing the viewer computer 500 with pathological images formed into tiles and guide data that will be described later. FIG. 5 is a diagram showing the functional blocks of the image management server 400.

The image management server 400 includes an image storing unit 41 (storage unit), an image providing unit 42, a guide data generating unit 43, a guide data storing unit 44 (storage unit), and a guide data providing unit 45.

The image storing unit 41 stores the pathological image. The pathological image is divided into images in a tile form with 256 by 256 pixels and held, and provided to the viewer computer 500 via the image providing unit 42 in response to an image request from the viewer computer 500.

The image providing unit 42 receives an image request from the viewer computer 500, acquires a pathological image corresponding to the image request from the image storing unit 41, and transmits the pathological image to the viewer computer 500.

The guide data generating unit 43 acquires the entire pathological image from the image storing unit 41 and generates guide data. The generation of the guide data is performed as batch processing at the time when the pathological image corresponding to one slide is obtained. The guide data is not generated in small steps in synchronization with the image request from the viewer computer 500. The generated guide data is stored in the guide data storing unit 44.

The guide data storing unit 44 stores the guide data of the pathological image, which has been generated by the guide data generating unit 43. The stored guide data is provided to the viewer computer 500 via the guide data providing unit 45 in response to a guide data request from the viewer computer 500.

The guide data providing unit 45 receives a guide data request from the viewer computer 500, acquires corresponding guide data from the guide data storing unit 44, and transmits the corresponding guide data to the viewer computer 500.

It should be noted that the image management server 400 and the viewer computer 500 form a client and server system, and thus it is a design matter to determine which function is provided to a client side and which function is provided to a server side. For that reason, the location where each of the functional blocks described above is executed is not limited to the image management server 400 described above, and a configuration in which the functional blocks are executed in the viewer computer 500 as a client side may also be provided.

[Functional Blocks of Viewer Computer 500]

Figure 6:
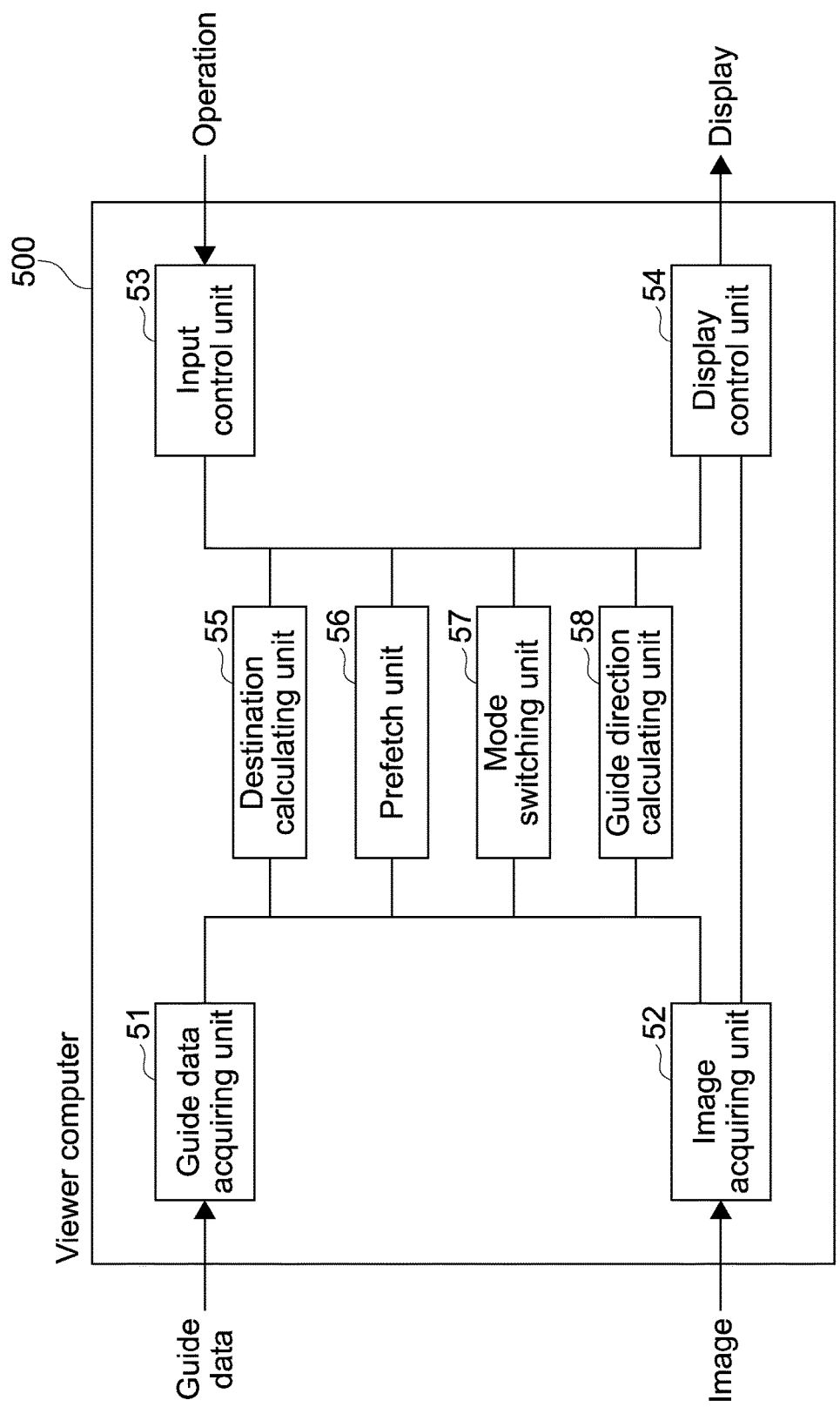
FIG. 6 A diagram showing the functional blocks of the viewer computer.

Next, the functional blocks of the viewer computer 500 will be described. The viewer computer 500 has a main function of receiving an operation instruction from a user who is a pathologist, acquiring a corresponding pathological image and guide data from the image management server 400, and presenting them to the user. FIG. 6 is a diagram showing the functional blocks of the viewer computer 500.

The viewer computer 500 includes a guide data acquiring unit 51, an image acquiring unit 52, an input control unit 53 (input unit), a display control unit 54 (display control unit), a destination calculating unit 55 (control unit), a prefetch unit 56 (control unit), a mode switching unit 57 (control unit), and a guide direction calculating unit 58 (control unit).

The guide data acquiring unit 51 acquires guide data, which will be described later, from the image management server 400. The guide data acquiring unit 51 acquires a pathological image that the user as a pathologist observes, from the image management server 400, to present the pathological image on the viewer computer 500. At that time, the guide data acquiring unit 51 first acquires guide data corresponding to the pathological image. The acquired guide data is passed to the destination calculating unit 55, the prefetch unit 56, and the guide direction calculating unit 58 and used in accordance with the respective intended uses.

The image acquiring unit 52 acquires a pathological image from the image management server 400, the pathological image being specified by the user to perform an observation. Further, the image acquiring unit 52 acquires an appropriate image from the image management server 400 each time a new image is required to be acquired, such as when the user rescales the pathological image or scrolls a display area.

The acquisition of the image is performed according to an operation of the user and also performed by prefetch by the prefetch unit 56. The image acquired from the image management server 400 is displayed on the display unit 26 via the display control unit 54.

The input control unit 53 interprets an operation made by the user and received by the operation input unit 24, for example, a keyboard and a mouse, and an operation received by the controller 30, for example, a game controller, via the interface unit 25, and gives an instruction to each related functional block.

For example, in the case where the scroll mode is the normal mode and when the controller 30 is tilted, the input control unit 53 recognizes a tilted direction and amount and gives an instruction to a related functional block so as to continuously scroll the image at a velocity corresponding to the tilt amount in that direction.

The display control unit 54 displays an image acquired from the image management server 400 by the image acquiring unit 52, a GUI (Graphical User Interface) with which the user inputs various operations, and the like on the screen of the display unit 26. Further, in the case where the scroll mode is the guide mode, the display control unit 54 displays an arrow, which will be described later, at a position and in a direction calculated by the guide direction calculating unit 58.

The destination calculating unit 55 calculates how a display range of the pathological image being currently displayed on the screen is moved, and from which position an image is to be newly read from the image management server when the display range is moved.

In the case where the scroll mode is the normal mode, the display range of a new screen is calculated in accordance with a scroll direction and a scroll amount that have been received by the operation of the controller 30 by the user. In the case where the scroll mode is the guide mode, the scroll direction and the scroll amount based on the guide data are calculated, and the display range of a new screen is obtained. A method of calculating the scroll direction and the scroll amount based on the guide data will be described later.

In order to smoothly display the image on the display unit 26, based on the display range of the current image or a user operation currently performed, the prefetch unit 56 prefetches a pathological image that is included in the display range predicted to be displayed next, from the image management server 400. The range of an image to be prefetched largely differs depending on whether the scroll mode is the normal mode or the guide mode. The range to be prefetched in each mode will be described later in detail.

The mode switching unit 57 receives a switching of the scroll mode from the user via the input control unit 53. Each time the user switches the scroll mode between the normal mode and the guide mode, the mode switching unit 57 gives an instruction to the destination calculating unit 55, the prefetch unit 56, and the guide direction calculating unit 58 and causes the destination calculating unit 55, the prefetch unit 56, and the guide direction calculating unit 58 to perform processing in accordance with each mode.

In the case where the scroll mode is the guide mode, the guide direction calculating unit 58 calculates a display position and a display direction of an arrow when an arrow indicating the scroll direction is displayed on the screen. The calculated display position and display direction are delivered to the display control unit 54, an arrow indicating the scroll direction is displayed at a predetermined position on the screen via the display control unit 54 and the display unit 26.

It should be noted that the viewer computer 500 and the image management server 400 form a client and server system as described above, and thus it is a design matter to determine which function is provided to a client side and which function is provided to a server side. For that reason, of the functional blocks described above, some locations where the functional blocks described above are executed are not limited to the viewer computer 500 described above, and a configuration in which the functional blocks are executed in the image management server 400 as a server side may be provided

[Problem and Solution when Needle Biopsy Image is Observed by Viewer]

Next, description will be given on a problem and a solution therefor when a needle biopsy image is observed by a viewer. First, a problem will be described. Conventionally, when an observation is performed along an elongated specimen whose image is captured as a needle biopsy image, the user has had to scroll the display range along the irregular shape of a specimen while fine-adjusting the scroll direction. So, the user has had to perform scrolling while fine-adjusting a stick operation of the controller 30, and there has been a problem that the user has a difficulty in focusing on an image diagnosis.

Figure 7:
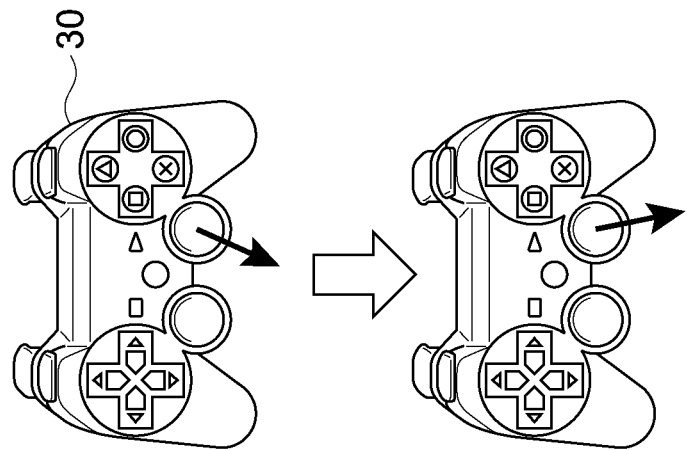
FIG. 7 A diagram showing an example of scrolling a display range while fine-adjusting a stick of the controller.
Figure 7:
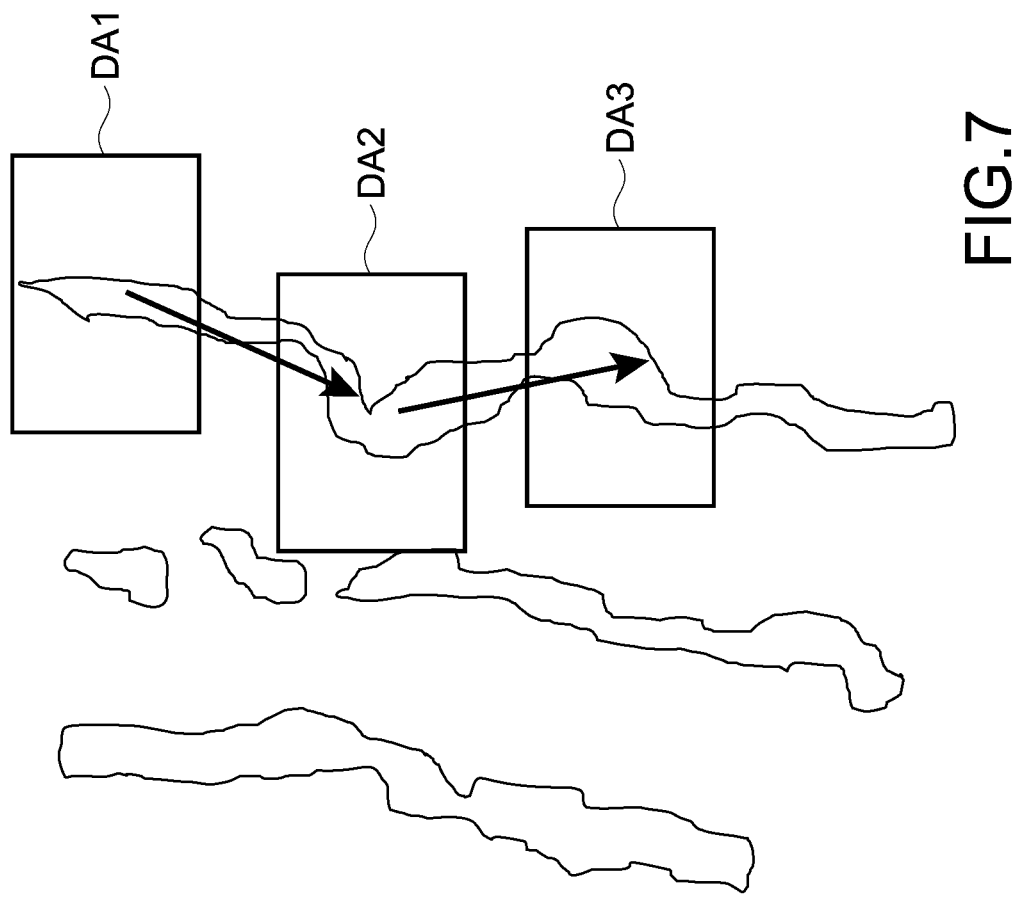

FIG. 7 is a diagram showing an example of scrolling the display range while fine-adjusting the stick of the controller 30. In order to scroll the display range from DA1 to DA2, the user tilts the stick of the controller 30 in a lower left direction and fine-adjusts the tilt direction such that the display range does not deviate from the specimen. In order to scroll the display range from DA2 to DA3, the user tilts the stick in a lower right direction and repeats fine adjustment in the same manner.

Next, a solution will be described. A solution is that the viewer computer 500 correctly scrolls the display range along the irregular shape of a specimen even when a scroll instruction by the user is roughly made.

By adopting such a method, for example, in the case of a specimen elongated in an upper and lower direction, the user only has to roughly input "upper direction" or "lower direction" as a scroll direction. Since the scrolling along the shape of the specimen is performed by the viewer computer 500, and thus the user is released from a task to finely operate a direction in which the stick of the controller 30 is tilted. For that reason, the user can focus on a diagnosis of the pathological image.

Further, since the scrolling by the viewer computer 500 is performed from end to end of the specimen, it is possible to prevent the user as a pathologist from overlooking a part of area of the specimen.

It should be noted that the scroll mode considered a solution is referred to as a guide mode here, and a conventional scroll mode in which the scrolling is performed in a free direction specified by the user is referred to a normal mode, for the purpose of distinction.

Figure 8:
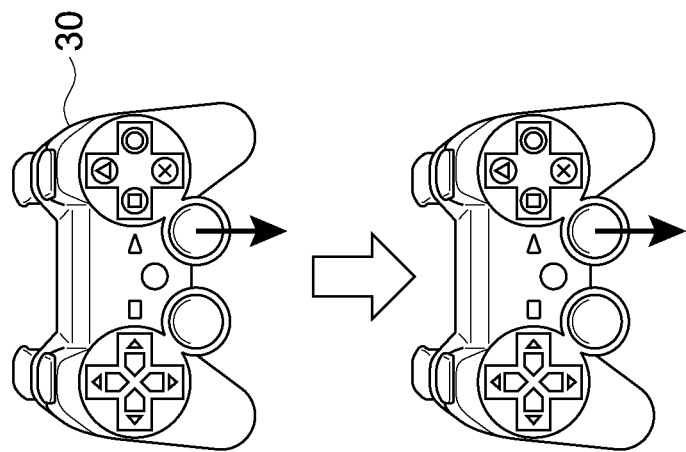
FIG. 8 A diagram showing an example of correctly scrolling the display range while roughly operating the stick of the controller.
Figure 8:
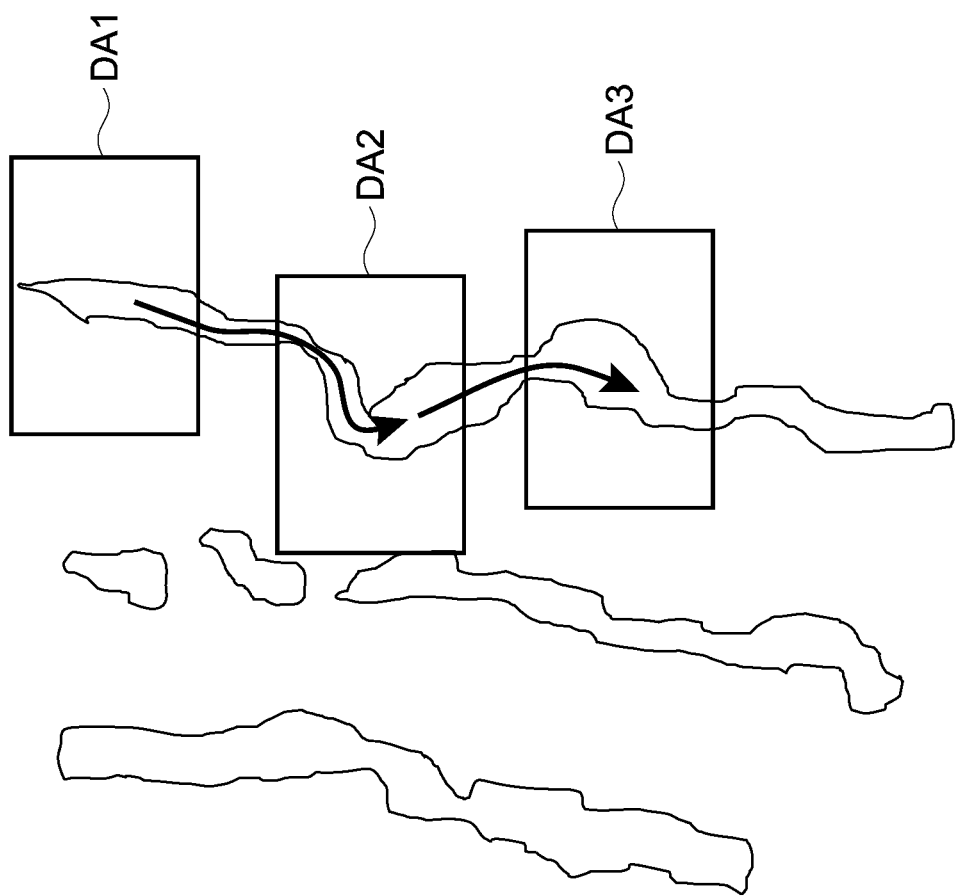

FIG. 8 is a diagram showing an example of correctly scrolling the display range while roughly operating the stick of the controller 30. The display range is first located at DA1 and is scrolled from DA1 to DA2 at the lower left. An operation made by the user at that time is tilting the stick of the controller 30 in a lower direction. The tilt direction may be any of a lower right direction, a lower left direction, or a just downward direction as long as the tilt direction may have an angle including a component of the lower direction. In this example, the user tilts the stick in the just downward direction.

Also in the case where the display range is scrolled from DA2 to DA3 at the lower right, an operation to be made by the user is merely tilting the stick in a lower direction. In this example, the user tilts the stick in the just downward direction, while the display range is scrolled to the lower right.

It should be noted that regarding details of a method of achieving the solution described above, the hardware and functional blocks to be provided to the image management server 400 and the viewer computer 500 are as described above. Other details will be described below.

[Regarding Guide Data]

Next, description will be given on guide data, which is a solution according to the present technology and is required to perform correct scrolling along the shape of a specimen by the viewer computer 500. It should be noted that the guide data refers to the aggregate of coordinates of point sequences that will be described below.

Figure 9:
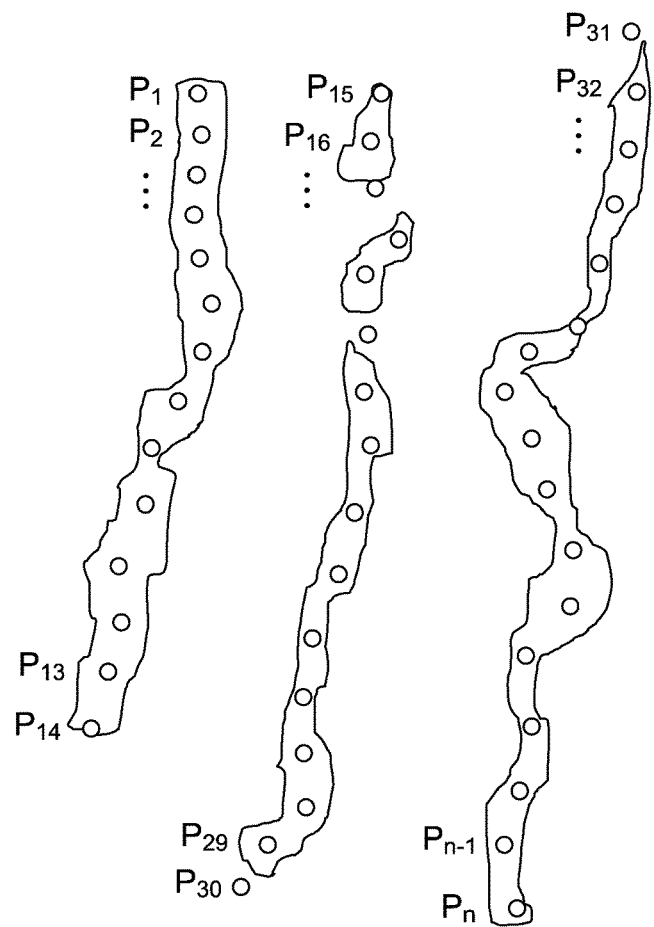
FIG. 9 A diagram showing an example in which a pathological image is subjected to an image analysis and a point sequence that serves as guide data is arranged on the specimen.

FIG. 9 is a diagram showing an example in which a pathological image is subjected to an image analysis and a point sequence that serves as guide data is arranged on a specimen. A method for the image analysis will be described later. In FIG. 9, three specimens are shown. A first point $P_1$ is located at the uppermost part of a specimen on the left-hand side. Starting from the first point $P_1$, points are determined at predetermined intervals along the center of the specimen, and a point $P_{14}$ is disposed at the lowermost part of the specimen on the left-hand side. The next point $P_{15}$ is located at the uppermost part of the center specimen, and similarly, $P_{30}$ is located at the lowermost part of the center specimen. A point $P_{31}$ subsequent to $P_{30}$ follows at the uppermost part of a specimen on the right-hand side, and Pn is disposed at the lowermost part.

It should be noted that in this example, point sequences Pn (n is an integer of 1 or more) are arranged in order from the left-hand side to the right-hand side of specimens each vertically arranged and from up to down of one specimen, but the arrangement way is not limited thereto as long as the specimens are arranged in order from the end.

In the following description, a line segment that connects adjacent points $P_j$ and $P_{j+1}$ (j=1, 2, . . . , n−1) of the point sequences Pn (n is an integer of 1 or more) is referred to as a point sequence line segment $P_jP_{j+1}$.

In the guide mode, the scrolling is performed such that a point Pn of the guide data or a point on the point sequence line segment comes to the center of the display range. It should be noted that in the following description, the center point of the display range is referred to as a view point.

[Calculation Method for Guide Data]

Next, description will be given on a calculation method for guide data, which is performed by the guide data generating unit 43 of the image management server 400. A method of obtaining the point sequence Pn (n is an integer of 1 or more) serving as guide data based on an analysis of a pathological image as an image of a specimen is not particularly limited as long as a point sequence Pn passing through the center line of the specimen is obtained.

Figure 10:
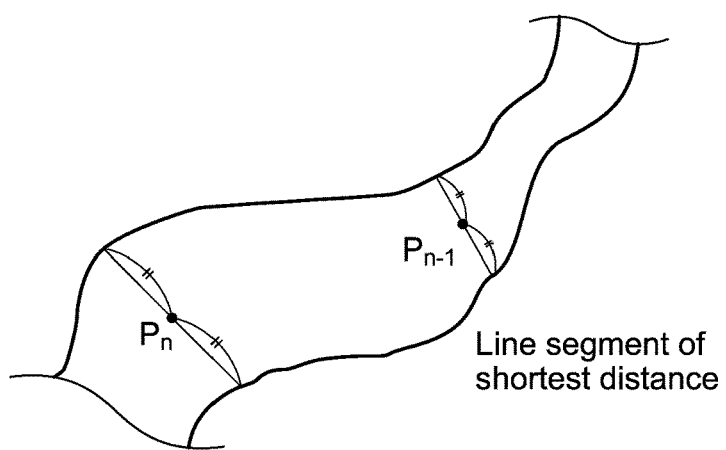
FIG. 10 A diagram showing an example of a case where a point Pn is obtained as a midpoint of the shortest line segment.

For example, in the vicinity of the center of an elongated specimen, among line segments connecting the outlines on both sides, a midpoint of the shortest line segment may be used to obtain the point sequence Pn. FIG. 10 is a diagram showing an example of a case where a point Pn is obtained as a midpoint of the shortest line segment.

Figure 11:
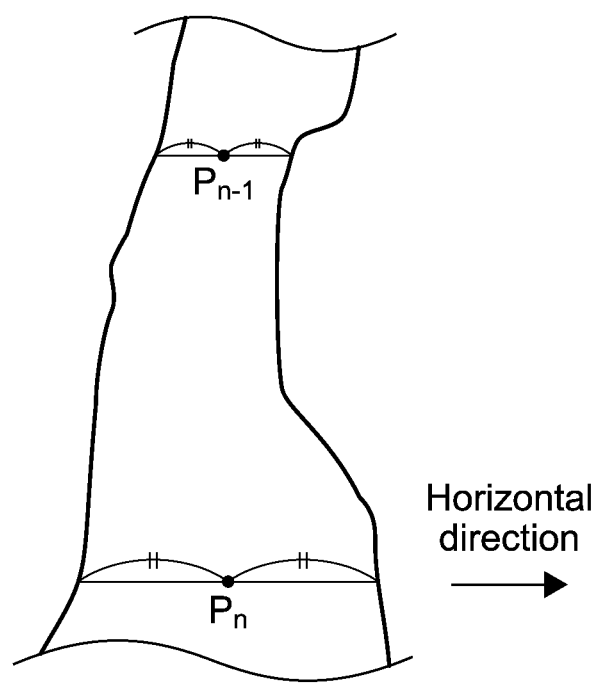
FIG. 11 A diagram showing an example of a case where a horizontal line is determined and a point Pn is obtained using the center point of the width in the horizontal direction of the specimen.

Further, for example, in the case where the point sequence Pn is obtained from a specimen vertically placed, a horizontal line that crosses the specimen in a horizontal direction may be determined first, and a point sequence Pn may be obtained using the center point of the width in the horizontal direction of the specimen. FIG. 11 is a diagram showing an example of a case where a horizontal line is determined and a point Pn is obtained using the center point of the width in the horizontal direction of the specimen.

[Method of Obtaining View Point Serving as Scroll Destination (Part 1)]

Next, description will be given on a method of obtaining, in the case where the scroll mode is the guide mode, a view point serving as a scroll destination of a display range in accordance with a direction and an amount in and by which the user operates the stick of the controller 30.

A method of setting the next view point is a method of obtaining, when the next view point candidate is obtained by a stick operation by the user, a point on a point sequence line segment, which is the closest from the coordinates of that view point candidate, and setting this point as the next view point. Using this method, even when the specimen is placed in a vertical direction or a transverse direction, the view point can be obtained adequately.

Figure 12:
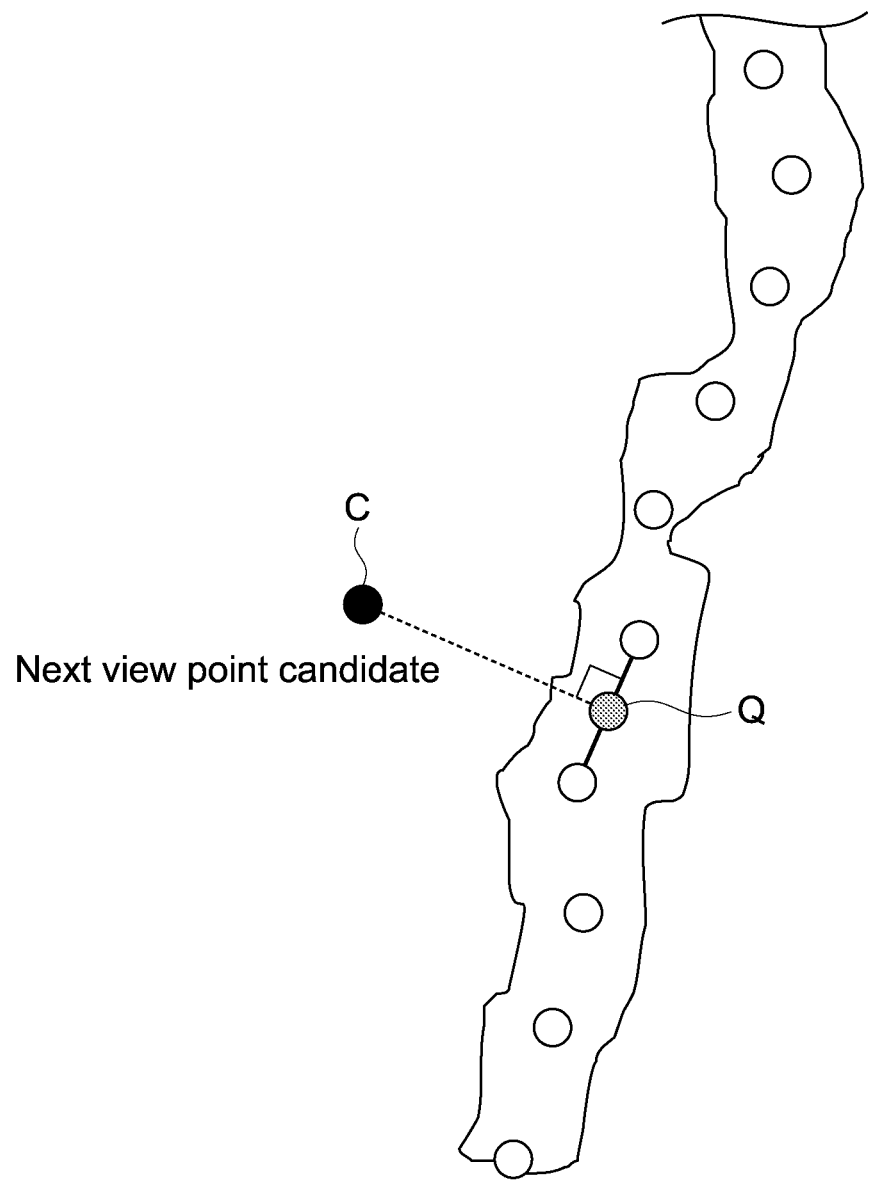
FIG. 12 A diagram showing an example of obtaining the next view point from view point candidates.

FIG. 12 is a diagram showing an example of obtaining the next view point from the view point candidates. A point Q on the point sequence line segment, which is the closest to the next view point candidate C, is determined as the next view point.

[Regarding Algorithm for Obtaining Point on Closest Line Segment]

Figure 13:
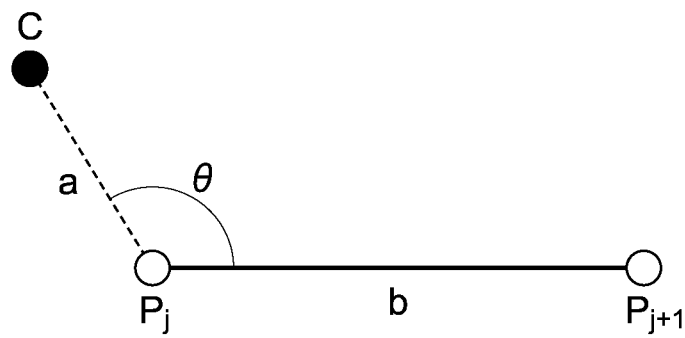
FIG. 13 A diagram showing an algorithm for obtaining a point Q on a point sequence line segment, which is the closest to a view point candidate C.
Figure 13:
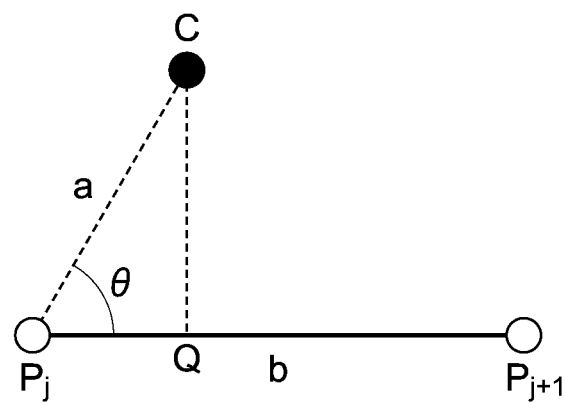
Figure 13:
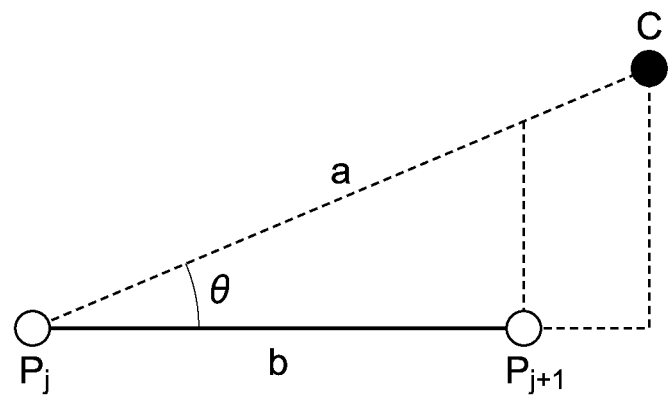

Next, description will be given on an algorithm for obtaining a point Q on a point sequence line segment, which is the closest to a view point candidate C. The description will be given with reference to FIG. 13. FIG. 13 is a diagram showing an algorithm for obtaining a point Q on a point sequence line segment, which is the closest to a view point candidate C.

First, when a point C as a view point candidate and a line segment $P_jP_{j+1}$ as one point sequence line segment are provided, an inner product a·b of a vector a connecting $P_jC$ and a vector b connecting $P_jP_{j+1}$ is calculated.

i) Case where a·b≤0

$$a \cdot b = |a||b|\cos \theta \leq 0, \text{ and thus } \cos \theta \leq 0.$$

So, $P_j$ is the closest point (see the upper diagram of FIG. 13).

ii) Case where a·b>0

If |a|cos θ≤|b|, Q is the closest point (see the middle diagram of FIG. 13).

If |a|cos θ>|b|, $P_{j+1}$ is the closest point (see the lower diagram of FIG. 13).

Next, the calculations described above are applied to the point C of the view point candidate and all the point sequence line segments $P_jP_{j+1}$ (j=1, 2, . . . , n−1) and a point at the shortest distance among them is obtained.

Lastly, the point obtained as a point at the shortest distance is set as the next view point.

[Method of Obtaining View Point Serving as Scroll Destination (Part 2)]

Figure 14:
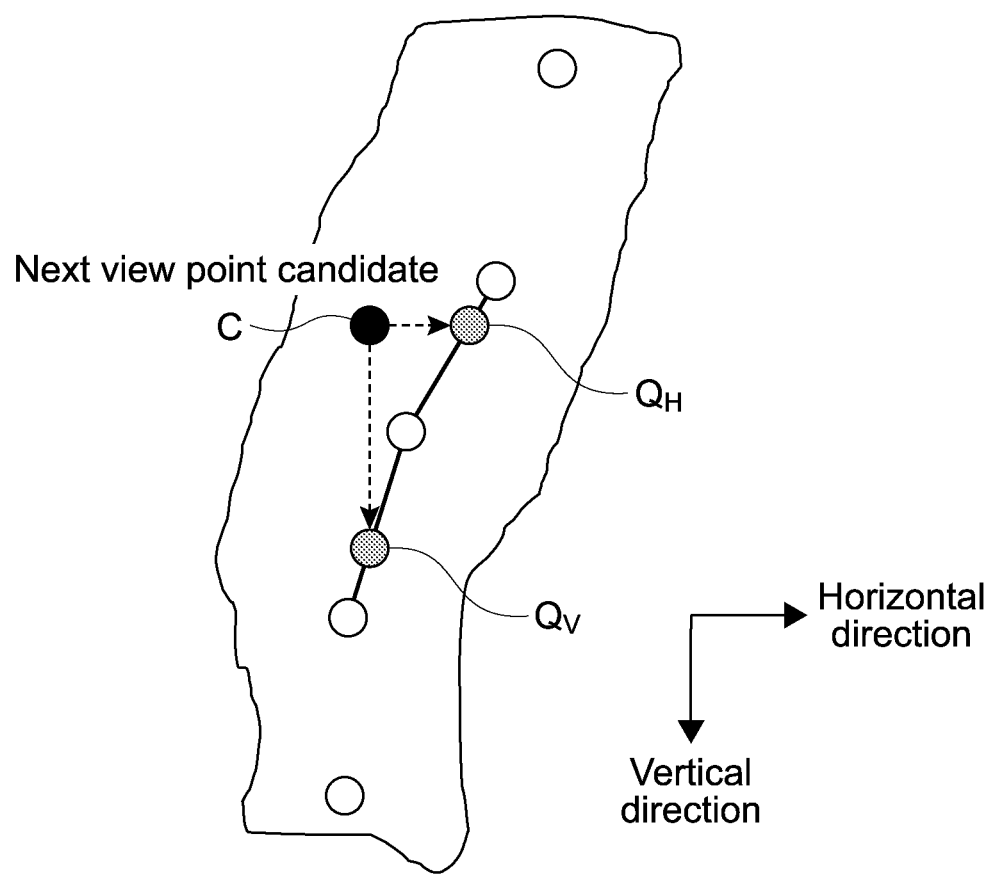
FIG. 14 A diagram for describing another algorithm for obtaining the next view point.

In the above description, the algorithm for determining the point Q on the point sequence line segment, which is the closest to the view point candidate C, as the next view point has been described. Here, a method of obtaining the next view point by using another algorithm will be described. FIG. 14 is a diagram for describing the other algorithm.

First, auxiliary lines are extended from the point C of the view point candidate toward a point sequence line segment in the horizontal direction and the vertical direction. A point at which the auxiliary line extended in the horizontal direction intersects the point sequence line segment is assumed as a point $Q_H$, and a point at which the auxiliary line extended in the vertical direction intersects the point sequence line segment is assumed as a point $Q_v$.

Next, the length of a line segment $CQ_H$ and the length of a line segment $CQ_v$ are compared, and a shorter one is selected. In FIG. 14, the line segment $CQ_H$ is selected because it is shorter.

Lastly, a point on the point sequence line segment, the point forming the selected line segment, is set as the next view point. In the example of FIG. 14, the point $Q_H$ is to be the next view point.

[Regarding Processing of Edge Point]

Figure 15:
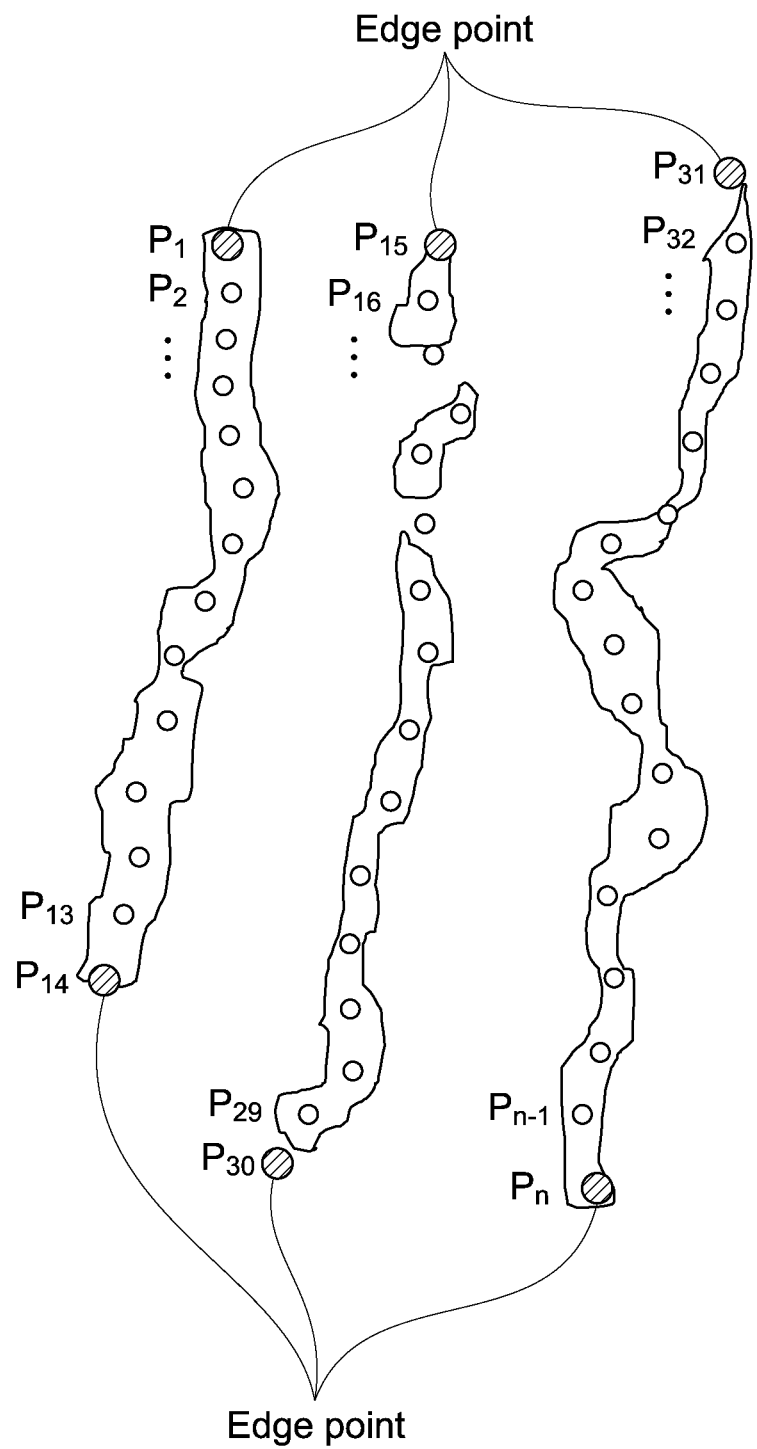
FIG. 15 A diagram showing which point is an edge point among points forming the point sequence.

Next, description will be given on processing of an edge point. The edge point refers to a point located at the end among points of a point sequence arranged on a specimen. FIG. 15 is a diagram showing which point is an edge point among points forming the point sequence. In FIG. 15, six points of $P_1$, $P_{14}$, $P_{15}$, $P_{30}$, $P_{31}$, and $P_n$ are edge points.

The processing of an edge point refers to, in FIG. 15 as an example, processing of moving the view point to the uppermost point $P_{15}$ of the center specimen without moving the next display range below $P_{14}$, when the view point comes down to the point $P_{14}$ of the specimen on the left-hand side.

The processing is performed in such a manner, and thus it is possible to significantly omit time and effort to search for an observed position, as compared with the case where the user observes a first specimen to the end and then searches for the end of the next specimen to start an observation again from that end.

It should be noted that the processing of an edge point is effective only in the case where the scroll mode is the guide mode.

[Regarding Display of Guide Line]

A guide line is a line obtained by displaying a point sequence line segment, as an actual line, on an image of a specimen.

Figure 16:
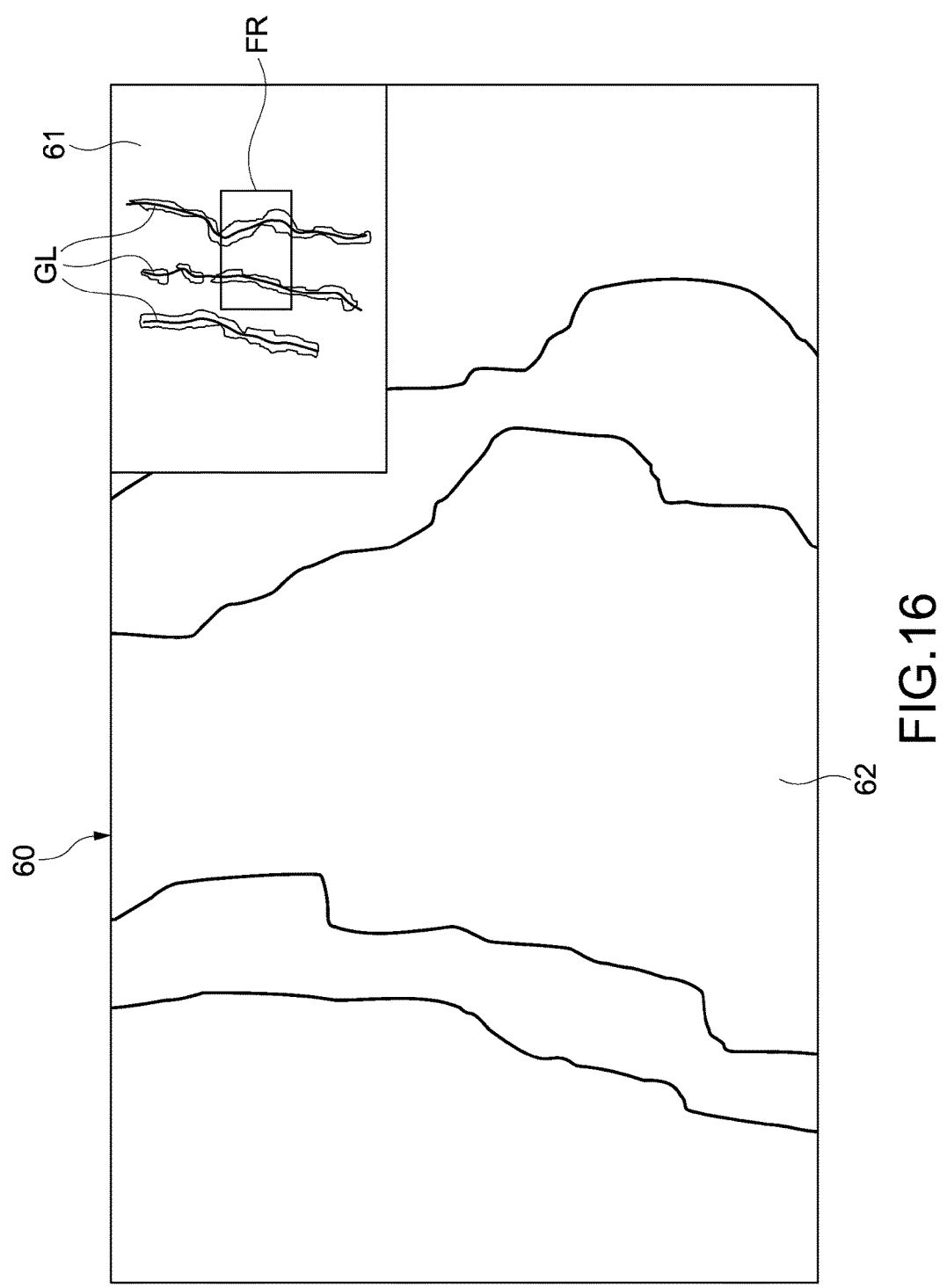
FIG. 16 A diagram showing an example in which a guide line is displayed on a viewer screen.

FIG. 16 is a diagram showing an example in which a guide line is displayed on a viewer screen. As shown in FIG. 16, a viewer screen 60 includes a thumbnail map 61 shown on the upper right of the viewer screen 60 and an observation area 62 for observing a pathological image. Shown on the thumbnail map 61 are a reduced-scale image of the entire image, a frame FR that equivalently shows on the thumbnail map 61 the range of the image being displayed in the observation area 62, and guide lines GL.

Each time an image displayed in the observation area 62 is scrolled by an instruction from the user, the frame FR is moved on the thumbnail map 61 in accordance with the scroll.

The guide lines GL are displayed on the thumbnail map 61, and thus the user can previously know how scrolling is performed in the case where the scroll mode is the guide mode.

It should be noted that the guide lines GL may also be displayed on the thumbnail map 61 when the scroll mode is the normal mode, without being limited to when the scroll mode is the guide mode. This is because the position of the center line of the specimen is known by the guide line GL.

Further, in the above description, the guide lines GL are displayed on the thumbnail map 61, but the present technology is not limited thereto and the guide lines GL may be configured to be displayed on the observation area 62. In the configuration in which the guide lines GL are displayed on the observation area 62, it is further desirable to provide a configuration capable of turning on and off display of the guide lines GL. This is because a diagnosis of an image by a pathologist is prevented from being interrupted by the guide lines GL.

[Regarding Switching of Scroll Mode]

The scroll mode when a pathological image displayed on the viewer screen is scrolled includes the normal mode and the guide mode as described above. In the normal mode, the user can perform scrolling by freely determining a scroll direction and a scroll amount, while in the guide mode, a scroll instruction by the user is corrected, and scrolling along the guide line is performed.

The switching between the normal mode and the guide mode is performed by an instruction from the user. For example, when the user performs an operation of pushing in the right-side stick of the controller 30, the input control unit 53 detects that operation and informs the mode switching unit 57 of the operation, and thus the mode switching unit 57 switches the scroll mode.

It should be noted that in the above description, the scroll mode is assumed to be switched between the normal mode and the guide mode. In such a case, the two modes do not coexist at the same time.

However, it may also be possible to adopt a configuration in which the both modes coexist. For example, although the user tilts the right-side stick of the controller 30 and thus scrolling prescribed in the guide mode is performed, subsequently, scrolling by which the center of the display range deviates from the view point may be performed by the user tilting the controller 30.

In such a manner, the mode switching unit 57 determines with which the operation by the user is performed, and thus the configuration in which the normal mode and the guide mode are automatically alternately switched can be adopted. With such a configuration, it is possible to omit time and effort for the user to give an instruction of switching the scroll mode.

[Regarding Display of Guide Direction]

In the above description, the guide lines GL shown on the thumbnail map 61 have been described as a method of showing, to the user, how scrolling is performed in the case where the scroll mode is the guide mode. As a method other than the above method, an arrow indicating a direction of a specimen, that is, a direction in which scrolling is performed in the guide mode, can be displayed in the observation area 62 of the viewer screen 60.

Figure 17:
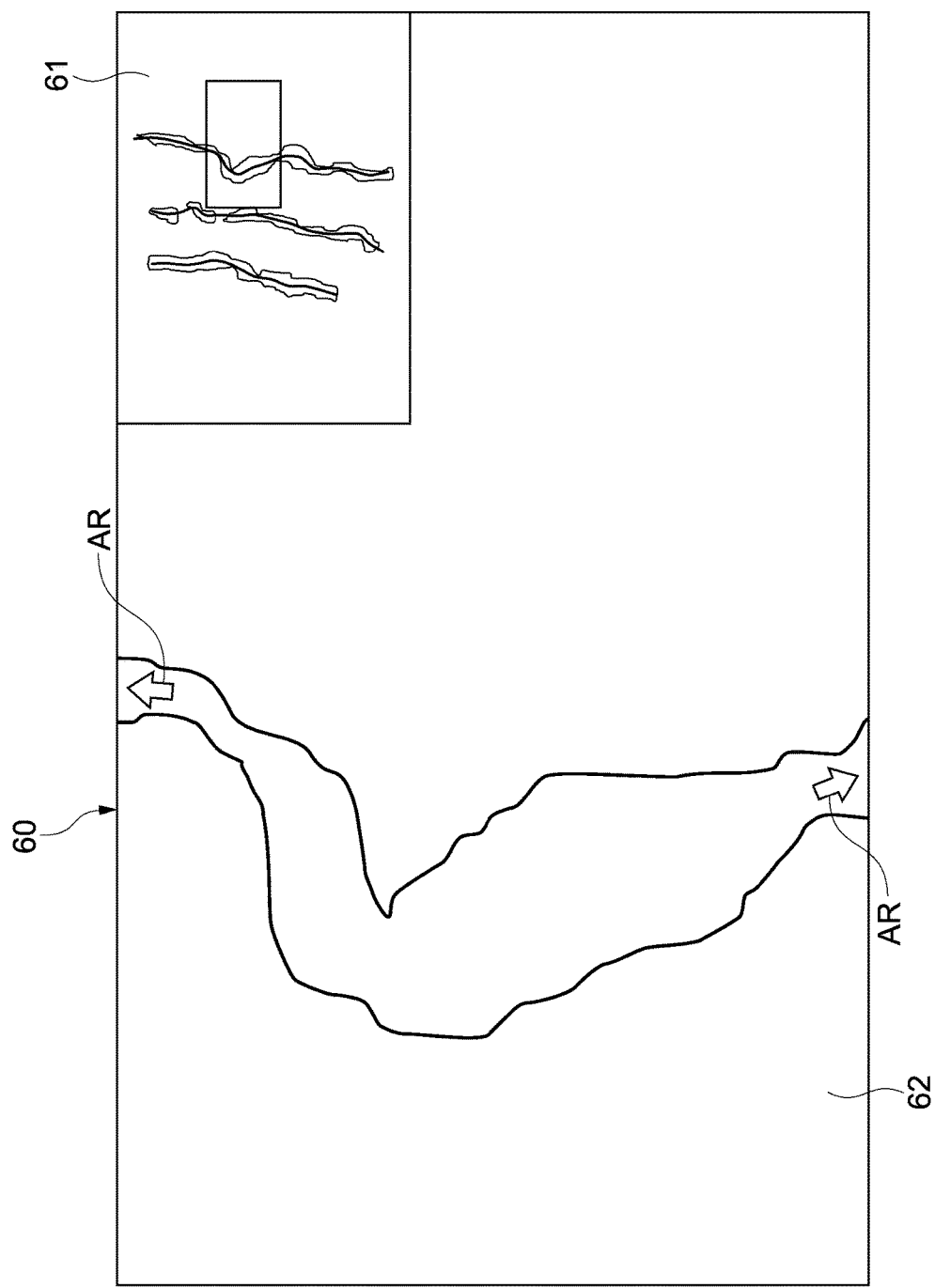
FIG. 17 A diagram showing an example in which an arrow AR indicating a scroll direction is displayed in an observation area of the viewer screen.

FIG. 17 is a diagram showing an example in which an arrow AR indicating a scroll direction is displayed in the observation area 62 of the viewer screen 60. FIG. 17 is the same as the viewer screen shown in FIG. 16 except the arrow AR, and description thereof will be omitted.

The arrow AR is displayed in the observation area 62, and thus the user can previously know in which direction scrolling of the image is performed in the guide mode. The arrow AR may be configured to be displayed not only in the guide mode but also in the normal mode. This is because, although the arrow AR indicates the scroll direction in the above description, the arrow AR simultaneously indicates in which direction out of the observation area 62 an image of a specimen extends as well, and thus information indicated by the arrow AR is useful also when the user performs free scrolling in the normal mode.

It should be noted that the display position and direction of the arrow AR are calculated by the guide direction calculating unit 58. Examples of a calculation method includes, in the case of the example shown in FIG. 17, a method of obtaining a point that is on a point sequence line segment passing on the specimen and at a predetermined distance from the edge of the observation area 42, and displaying an arrow on the point in conformity to a direction of the point sequence line segment.

[Summary of Scroll Method]

Figure 18:
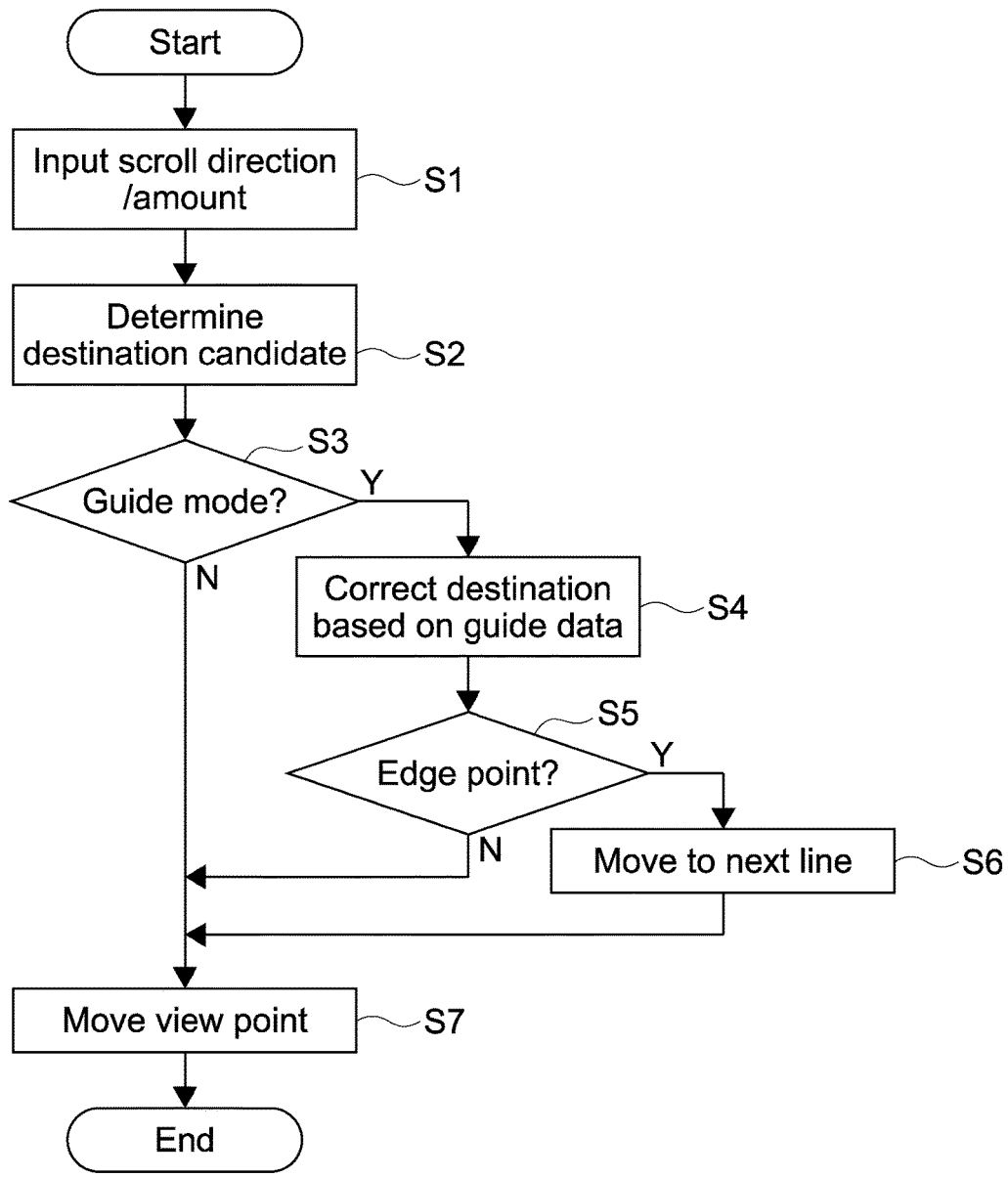
FIG. 18 A flowchart showing a flow of a scroll method.

Here, the flow of the scroll method for an image is summarized. FIG. 18 is a flowchart showing the flow of the scroll method.

First, the input control unit 53 detects a tilt of the controller 30 or a tilt of a stick on the controller 30 and receives a scroll direction and a scroll amount that the user inputs (Step S1).

Next, the destination calculating unit 55 calculates a destination candidate of the view point (Step S2).

In the case where the scroll mode is the normal mode (N of Step S3), the destination candidate calculated in Step S2 is set to be the next view point without change. In the case where the scroll mode is the guide mode when a destination of the view point is calculated (Y of Step S3), the destination of the view point is corrected to set the next view point based on the guide data (Step S4).

In the case where the destination of the view point is an edge point (Y of Step S5), an edge point on the next specimen (line) is set to be the next view point (Step S6).

Lastly, the display control unit 54 acquires an image corresponding to the next view point from the image management server 400 via the image acquiring unit 52, and performs actual scrolling to the set next view point (Step S7).

Along the flow described above, the scrolling of the pathological image is performed.

[Regarding Prefetch of Image]

Next, the prefetch of an image will be described.

The prefetch of an image is normally performed in order to display a new display range in scrolling at high speed. The periphery of the current display range is prefetched and stored in a cache, and thus speeding up of display can be achieved.

Figure 19:
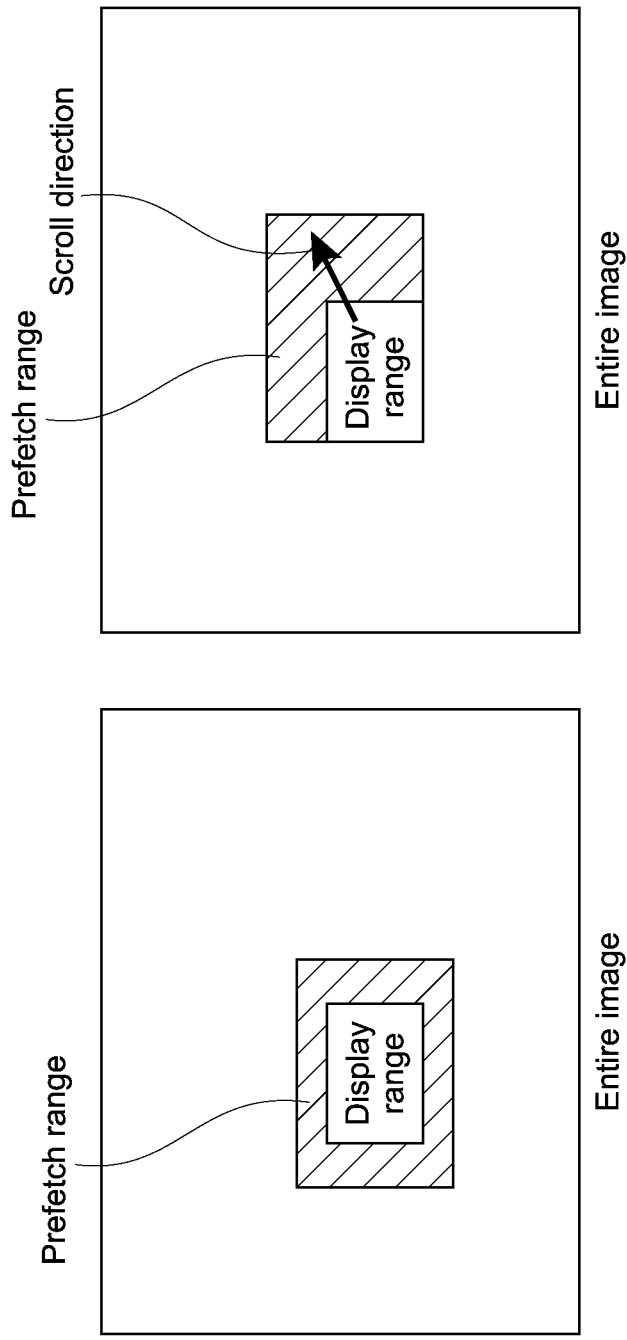
FIG. 19 A diagram showing a prefetch target range.

A prefetch range largely differs depending on circumstances. FIG. 19 is a diagram showing a prefetch target range. For example, during rest in which a certain area is displayed and no scroll operation is performed, as shown on the left-hand side of FIG. 19, the whole of the periphery of the currently displayed area is a prefetch target. Further, as shown on the right-hand side of FIG. 19, in the case where a scroll operation is performed from a state where a certain area is displayed, because of a scroll direction toward the upper right, a range to be a prefetch target is the right side and upper side of the currently displayed area.

In such a manner, the range on which prefetch is performed largely differs depending on circumstances and a destination of the display range is not necessarily as predicted. So, a prefetched image is not used in some cases and a prefetch efficiency (prefetch cache hit ratio) is not always good.

However, in the case of the scrolling in the guide mode according to the present technology, circumstances are different. The view point as the center of the display range when scrolling is performed only moves on a point sequence line segment, that is, in one axis direction on the guide line GL, and a prediction on the next display range can be easily and reliably performed. For that reason, the prefetch cache hit ratio is high, and prefetching becomes very effective means for speeding up of display.

Figure 20:
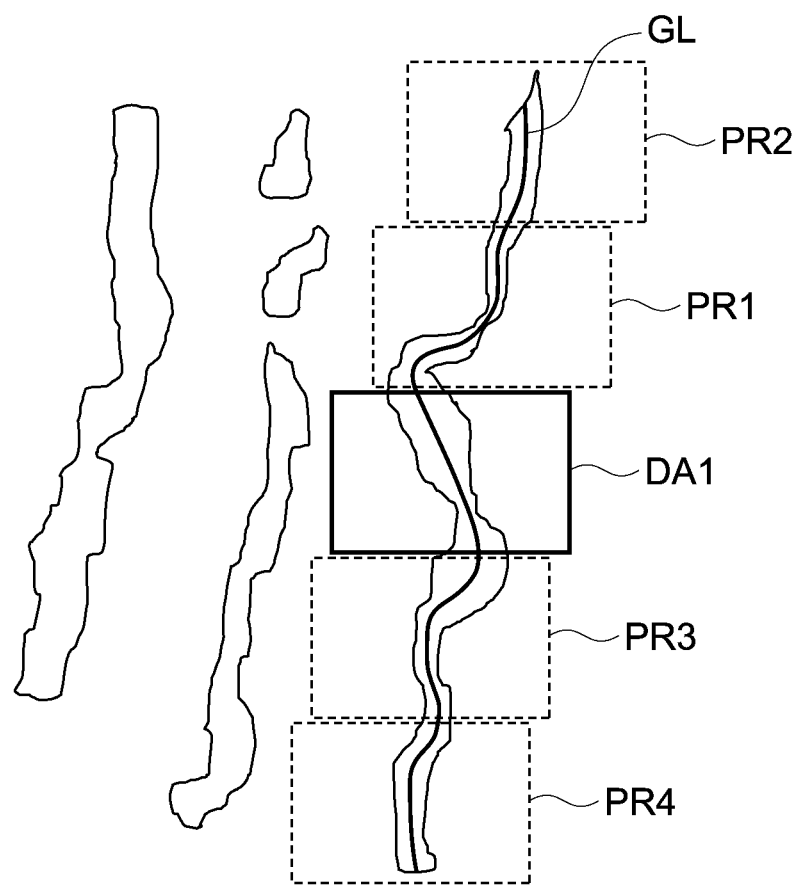
FIG. 20 A diagram showing a specific example of prefetch.

FIG. 20 is a diagram showing a specific example of prefetch. Areas along the guide line GL in the upper and lower directions when seen from the current display range DA1 are prefetch ranges PR1, PR2, PR3, and PR4.

Figure 21:
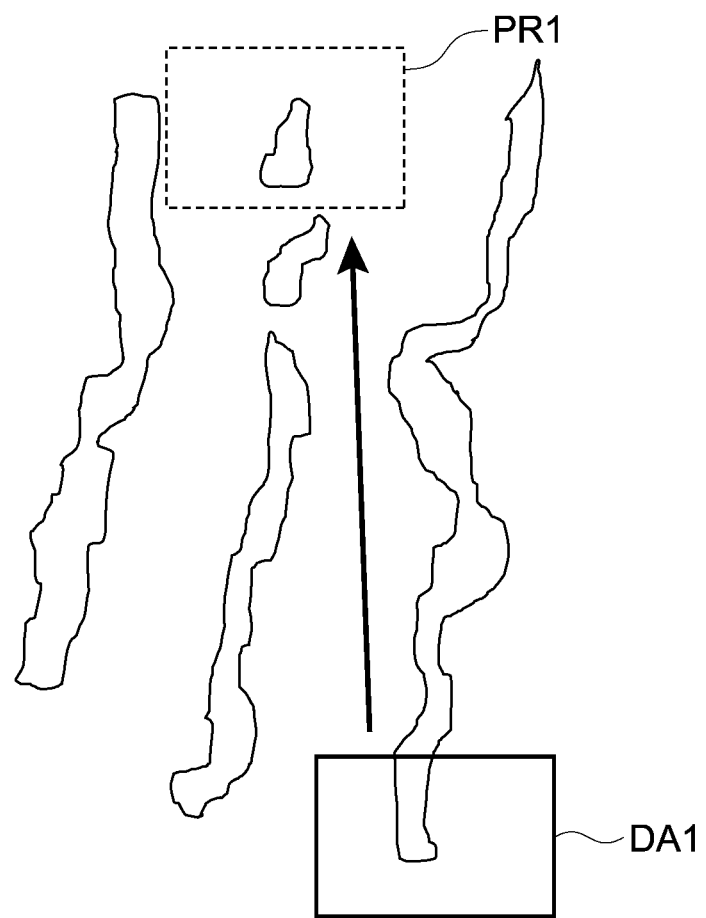
FIG. 21 A diagram showing a prefetch range PR1 in the case where a view point of a current display range DA1 is put on an edge point.

It should be noted that as shown in FIG. 21, even in the case where the view point of the current display range DA1 is put on an edge point, the prefetch range PR1 can be correctly read.

[Regarding Flow of Prefetch Processing]

Figure 22:
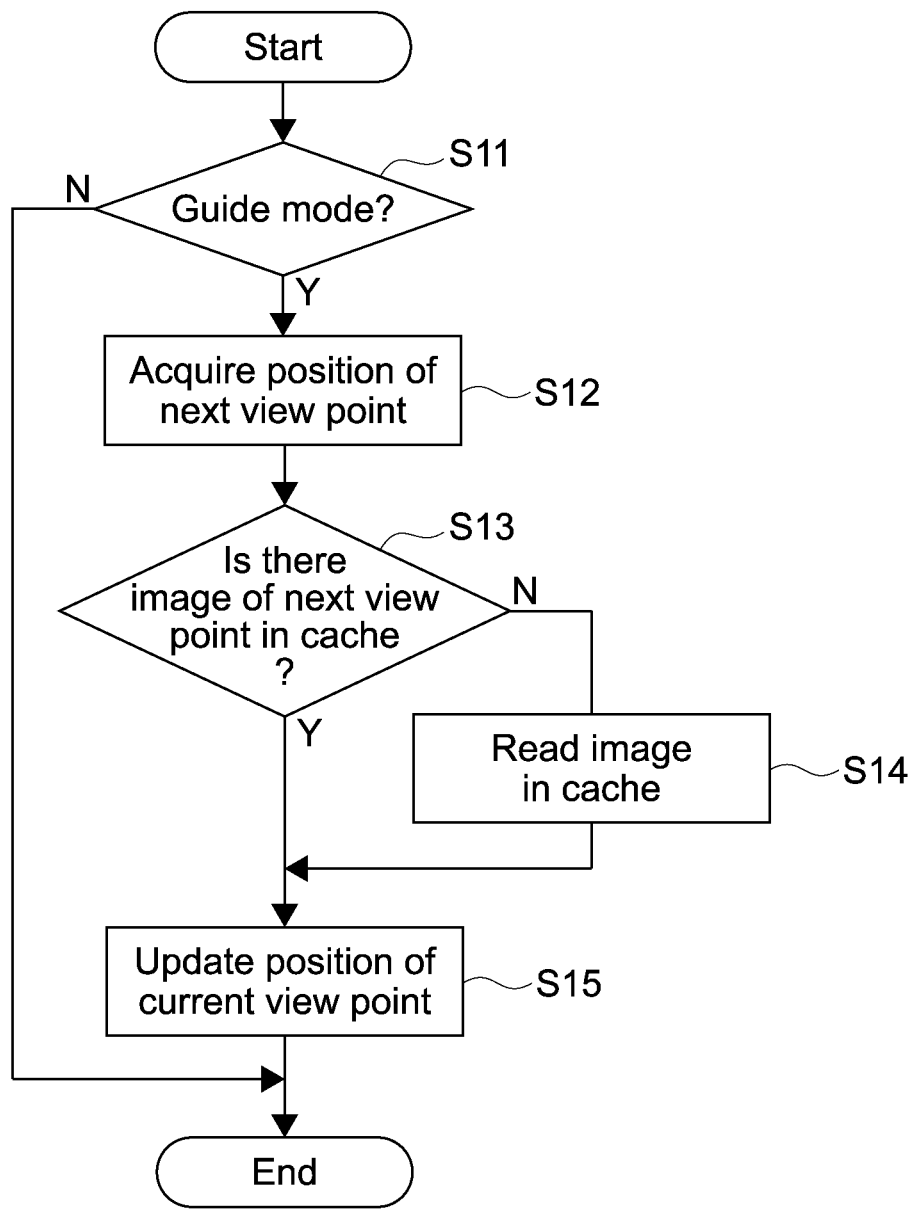
FIG. 22 A flowchart showing a flow of prefetch processing.

Next, the flow of prefetch processing will be described. FIG. 22 is a flowchart showing the flow of the prefetch processing.

First, the prefetch unit 56 determines whether the current scroll mode is the guide mode or not (Step S11). In the case where the current scroll mode is not the guide mode (N of Step S11), the processing is terminated without any operation.

Next, the prefetch unit 56 acquires a position of the next view point from the destination calculating unit 55 (Step S12).

Next, the prefetch unit 56 checks whether an image corresponding to the position of the next view point is in the cache or not (Step S13). If the image is not in the cache (N of Step S13), an image is prefetched anew (Step S14).

Lastly, the position of the current view point is updated using the position of the next view point (Step S15).

The above is the flow of the processing when prefetch is performed. It should be noted that in Step S11, in the case where the scroll mode is not the guide mode, the processing is terminated without doing any operation. In the normal mode as well, however, a configuration for performing the prefetch processing may be adopted, though the efficiency becomes poor.

[Regarding Effect by Prefetch]

Effects by prefetching in the case where the scroll mode is the guide mode will be described.

First, as described above, since the prefetch cache hit ratio is raised, the feeling of use of the viewer in the case where the network 300 used by the viewer computer 500 is in a low throughput environment is improved.

Further, since the prefetch of useless image data is reduced, a network bandwidth can be effectively used.

[Regarding Other Prefetch Examples]

In the above description, the method of prefetching an image along the guide line GL in the guide mode has been described. In addition thereto, in a pathological diagnosis, as a method of prefetching an image, for example, a method of learning a habit of a pathologist and performing prefetch based on the habit is conceived. Further, there is also conceived preferentially prefetching the vicinity of a part on which an annotation is put on a pathological image.

Furthermore, there is conceived a case where a prefetch reliability is obtained as a level of a predicted hit ratio of prefetch cache, and when the prefetch reliability is high, many prefetch images are requested to the image management server 400 at a time. In this case, many images are transmitted together, and thus a transmission efficiency can be improved.

[Another Configuration of Present Technology]

It should be noted that the present technology can also have the following configurations.

(1) An information processing apparatus, including:

a storage unit to store a pathological image of a specimen and guide information along the center line of a shape of the specimen in the pathological image;

a display control unit to display at least a part of the stored pathological image, as an observation image, on a screen;

an input unit to receive an instruction for changing a range on the pathological image of the observation image displayed on the screen, from a user; and a control unit to calculate the range on the pathological image of the observation image based on the instruction and the stored guide information.

(2) The information processing apparatus according to (1), in which the guide information is an arrangement of positional information on the pathological image, the positional information including points that are set on the entire specimen at predetermined intervals on the center line of the specimen on the pathological image.

(3) The information processing apparatus according to (1) or (2), in which the control unit assumes the center point of the range on the pathological image of the observation image, as a first center point, the range being calculated based on only the instruction, and assumes a point corresponding to the first center point and being on a line segment connecting adjacent points included in the guide information, as a second center point, to calculate the range on the pathological image of the observation image including the second center point.

(4) The information processing apparatus according to any one of (1) to (3), in which the control unit assumes a point that is on the line segment and is the closest to the first center point, as the second center point.

(5) The information processing apparatus according to any one of (1) to (3), in which the control unit assumes, as the second center point, a point that is the closest to the first center point among points at which auxiliary lines extended from the first center point in a horizontal direction and a vertical direction intersect the line segment.

(6) The information processing apparatus according to any one of (1) to (5), in which the control unit prefetches the observation image from the storage unit, the observation image being predicted based on the guide information and the instruction predicted to be received by the input unit.

(7) The information processing apparatus according to any one of (1) to (6), in which the control unit switches between a guide mode in which the range on the pathological image of the observation image is calculated based on the instruction and the guide information, and a normal mode in which the range on the pathological image of the observation image is calculated based on only the instruction.

(8) The information processing apparatus according to (7), in which the control unit switches between the guide mode and the normal mode based on a mode switching instruction that is explicitly made by the user and received by the input unit.

(9) The information processing apparatus according to (7), in which the control unit assumes, as a first input method, a method of inputting the instruction received by the input unit in the guide mode and assumes, as a second input method, a method of inputting the instruction that is different from the first input method and is received by the input unit in the normal mode, determines by which of the input methods the instruction is input, and switches between the guide mode and the normal mode based on the determination.

(10) The information processing apparatus according to any one of (1) to (9), in which, the display control unit displays an arrow indicating a position and a direction followed by a part of the specimen that deviates from the observation image, on the screen on which a part of the specimen is displayed as the observation image.

(11) The information processing apparatus according to any one of (1) to (10), in which the display control unit displays the guide information on the screen.

(12) The information processing apparatus according to any one of (1) to (10), in which the display control unit displays the guide information on a thumbnail map in which the entire pathological image is displayed.

(13) The information processing apparatus according to any one of (1) to (12), further including a controller including a tilt sensor, in which the user inputs the instruction by tilting the controller.

(14) The information processing apparatus according to any one of (1) to (13), in which the guide information causes, in a case where a plurality of specimens are imaged on the pathological image, the control unit to calculate the range on the pathological image such that the observation image of an end of one of the specimens is followed by an end of another specimen to be the observation image.

(15) An information processing method, including:

storing, by a storage unit, a pathological image of a specimen and guide information along the center line of a shape of the specimen in the pathological image;

displaying, by a display control unit, at least a part of the stored pathological image, as an observation image, on a screen;

receiving, by an input unit, an instruction for changing a range on the pathological image of the observation image displayed on the screen, from a user; and calculating, by a control unit, the range on the pathological image of the observation image based on the instruction and the stored guide information.

(16) An information processing program causing a computer to operate as:

a storage unit to store a pathological image of a specimen and guide information along the center line of a shape of the specimen in the pathological image;

a display control unit to display at least a part of the stored pathological image, as an observation image, on a screen;

an input unit to receive an instruction for changing a range on the pathological image of the observation image displayed on the screen, from a user; and a control unit to calculate the range on the pathological image of the observation image based on the instruction and the stored guide information.

(17) An information processing system, including:

a server computer including a storage unit to store a pathological image of a specimen and guide information along the center line of a shape of the specimen in the pathological image, and a providing unit to provide the stored pathological image and the stored guide information to a client computer; and the client computer including an acquiring unit to acquire the pathological image and the guide information from the server computer, a display control unit to display at least a part of the acquired pathological image, as an observation image, on a screen, an input unit to receive an instruction for changing a range on the pathological image of the observation image displayed on the screen, from a user, and a control unit to calculate the range on the pathological image of the observation image based on the instruction and the acquired guide information.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

DESCRIPTION OF REFERENCE NUMERALS 10 microscope
20 scanner computer
21 CPU
22 ROM
23 RAM
24 operation input unit
25 interface unit
26 display unit
27 storage unit
28 network interface unit
29 bus
30 controller
41 image storing unit
42 image providing unit
43 guide data generating unit
44 guide data storing unit
45 guide data providing unit
51 guide data acquiring unit
52 image acquiring unit
53 input control unit
54 display control unit
55 destination calculating unit
56 prefetch unit
57 mode switching unit
58 guide direction calculating unit
60 viewer screen
61 thumbnail map
62 observation area
100 scanner
300 network
400 image management server
500 viewer computer

The invention claimed is:

1. An information processing apparatus, comprising:
a memory configured to store a pathological image of an elongated specimen, wherein the pathological image is captured as a virtual slide; and
a central processing unit (CPU) configured to:
generate guide information that comprises a plurality of points at intervals along a center line of a shape of the elongated specimen in the pathological image, wherein the center line includes the plurality of points which are connected by a plurality of line segments;
control a display device to display a first part of the pathological image, based on the generated guide information, as an observation image, wherein a center point of the observation image comprises a first view point;
receive an instruction to change a first display range on the first part of the pathological image of the observation image, displayed on the display device, wherein the instruction comprises a view point candidate for a second display range for the observation image;
set a display mode of the display device as one of a normal mode or a guide mode,
wherein, in the normal mode, a second part of the pathological image is set based on the first part of the pathological image and the instruction, and
wherein, in the guide mode, the second part of the pathological image is set based on the first part of the pathological image, the instruction, and the generated guide information;
calculate the second display range on the second part of the pathological image of the observation image based on the instruction and the generated guide information,
wherein the second display range is calculated based on a setting operation to set a second view point that is closest to the view point candidate, and
wherein the second view point lies on a line segment of the plurality of line segments in the guide information; and
control the display device to display the observation image that is centered on the second view point.

2. The information processing apparatus according to claim 1,
wherein the generated guide information is an arrangement of positional information on the pathological image, and
wherein the arrangement of positional information includes the plurality of points that are set on the elongated specimen.

3. The information processing apparatus according to claim 2, wherein the CPU is further configured to:
determine a center point of the first display range on the pathological image of the observation image, as a first center point, wherein the first display range is calculated based on the instruction,
determine a first point corresponding to the first center point on the line segment that connects adjacent points included in the generated guide information, as a second center point, and
calculate the second display range on the pathological image of the observation image based on the first center point and the second center point, wherein the second display range includes the second center point.

4. The information processing apparatus according to claim 3, wherein the CPU is further configured to determine a second point on the line segment closest to the first center point, as the second center point.

5. The information processing apparatus according to claim 3,
wherein the CPU is further configured to determine, as the second center point, a third point closest to the first center point among the plurality of points, and
wherein auxiliary lines extended from the first center point in a horizontal direction and a vertical direction intersect the line segment at the third point.

6. The information processing apparatus according to claim 1,
wherein the CPU is further configured to fetch the observation image from the memory, and wherein the observation image is determined based on the generated guide information and the instruction.

7. The information processing apparatus according to claim 6, wherein the CPU is further configured to switch between the guide mode and the normal mode,
wherein, in the normal mode, the CPU is further configured to calculate the second display range on the second part of the pathological image of the observation image based on the instruction.

8. The information processing apparatus according to claim 7, wherein the CPU is further configured to switch between the guide mode and the normal mode based on a mode switching instruction.

9. The information processing apparatus according to claim 7, wherein the CPU is further configured to:
determine a first input method configured to input a first instruction received in the guide mode,
determine a second input method configured to input a second instruction, different from the first instruction, received in the normal mode, and
switch between the guide mode and the normal mode based on the determination of one of the first input method or the second input method.

10. The information processing apparatus according to claim 8, wherein the CPU is further configured to control the display device to display an arrow, and wherein the arrow indicates a position and a direction followed by a part of the elongated specimen that deviates from the observation image.

11. The information processing apparatus according to claim 10, wherein the CPU is further configured to control the display device to display the generated guide information.

12. The information processing apparatus according to claim 11, wherein the CPU is further configured to control the display device to display the generated guide information on a thumbnail map, wherein the thumbnail map is configured to display the pathological image.

13. The information processing apparatus according to claim 12, further comprising a controller including a tilt sensor, wherein the tilt sensor is configured to input the instruction based on a detection of a tilt of the controller.

14. The information processing apparatus according to claim 13, wherein, based on a plurality of specimens in the pathological image and the generated guide information, the CPU is further configured to:
calculate the second display range on the second part of the pathological image such that the observation image of a first end of a first specimen of the plurality of specimens is followed by a second end of a second specimen of the plurality of specimens of the observation image.

15. An information processing method, comprising:
in an information processing apparatus:
storing a pathological image of an elongated specimen, wherein the pathological image is captured as a virtual slide;
generating guide information that comprises a plurality of points at intervals along a center line of a shape of the elongated specimen in the pathological image,
wherein the center line includes the plurality of points are connected by a plurality of line segments;
controlling a display device to display a first part of the pathological image, based on the generated guide information, as an observation image,
wherein a center point of the observation image comprises a first view point;

receiving an instruction for changing a first display range on the first part of the pathological image of the observation image, displayed on the display device, wherein the instruction comprises a view point candidate for a second display range for the observation image;

setting a display mode of the display device as one of a normal mode or a guide mode,
  wherein, in the normal mode, a second part of the pathological image is set based on the first part of the pathological image and the instruction, and
  wherein, in the guide mode, the second part of the pathological image is set based on the first part of the pathological image, the instruction, and the generated guide information;

calculating the second display range on the second part of the pathological image of the observation image based on the instruction and the generated guide information,
  wherein the second display range is calculated based on a setting operation to set a second view point closest that is to the view point candidate, and
  wherein the second view point lies on a line segment of the plurality of line segments in the guide information; and controlling the display device to display the observation image that is centered on the second view point.

16. A non-transitory computer-readable medium having stored thereon, computer-executable instructions, which when executed by a processor in an information processing apparatus, cause the processor to execute operations, the operations comprising:

storing a pathological image of an elongated specimen in a memory, wherein the pathological image is captured as a virtual slide;

generating guide information that comprises a plurality of points at intervals along a center line of a shape of the elongated specimen in the pathological image,
  wherein the center line includes the plurality of points are connected by a plurality of line segments;

controlling a display device to display a first part of the pathological image, based on the generated guide information, as an observation image,
  wherein a center point of the observation image comprises a first view point;

receiving an instruction for changing a first display range on the first part of the pathological image of the observation image, displayed on the display device, wherein the instruction comprises a view point candidate for a second display range for the observation image;

setting a display mode of the display device as one of a normal mode or a guide mode,
  wherein, in the normal mode, a second part of the pathological image is set based on the first part of the pathological image and the instruction, and
  wherein, in the guide mode, the second part of the pathological image is set based on the first part of the pathological image, the instruction, and the generated guide information;

calculating the second display range on the second part of the pathological image of the observation image based on the instruction and the generated guide information,
  wherein the second display range is calculated based on a setting operation to set a second view point that is closest to the view point candidate, and
  wherein the second view point lies on a line segment of the plurality of line segments in the guide information; and controlling the display device to display the observation image that is centered on the second view point.

17. An information processing system, comprising:

a server computer including:
  first circuitry configured to:
    store a pathological image of an elongated specimen in a memory, wherein the pathological image is captured as a virtual slide;
    generate guide information that comprises a plurality of points at intervals along a center line of a shape of the elongated specimen in the pathological image,
      wherein the center line includes the plurality of points are connected by a plurality of line segments; and
    transmit the pathological image and the generated guide information to a client computer; and the client computer including:
  second circuitry configured to:
    acquire the pathological image and the generated guide information from the server computer;
    control a display device to display a first part of the pathological image, based on the generated guide information, as an observation image,
      wherein a center point of the observation image comprises a first view point;
    receive an instruction to change a first display range on the first part of the pathological image of the observation image, displayed on the display device, wherein the instruction comprises a view point candidate for a second display range the observation image;
    set a display mode of the display device as one of a normal mode or a guide mode,
      wherein, in the normal mode, a second part of the pathological image is set based on the first part of the pathological image and the instruction, and
      wherein, in the guide mode, the second part of the pathological image is set based on the first part of the pathological image, the instruction, and the generated guide information;
    calculate a second display range on the second part of the pathological image of the observation image based on the instruction and the generated guide information,
      wherein the second display range is calculated based on a setting operation to set a second view point that is closest to the view point candidate, and
      wherein the second view point lies on a line segment of the plurality of line segments in the guide information; and
    control the display device to display the observation image that is centered on the second view point.

* * * * *